United States Patent [19]

Kramer

[11] Patent Number: 5,431,880
[45] Date of Patent: Jul. 11, 1995

[54] LIGHT TRANSMITTANCE TYPE ANALYTICAL SYSTEM AND VARIABLE TRANSMITTANCE OPTICAL COMPONENT AND TEST DEVICE FOR USE THEREIN

[76] Inventor: Donald L. Kramer, 1340 SW. 19th Ave., Boca Raton, Fla. 33487

[21] Appl. No.: 812,716

[22] Filed: Dec. 23, 1991

Related U.S. Application Data

[63] Continuation-in-part of Ser. No. 559,252, Jul. 30, 1990, abandoned, which is a continuation of Ser. No. 69,960, Jul. 6, 1987, abandoned.

[51] Int. Cl.$^6$ ............................................. G01N 21/59
[52] U.S. Cl. ........................................ 422/56; 422/55; 422/57; 422/66; 422/67; 436/164; 436/166; 436/169; 436/170; 436/172
[58] Field of Search ............... 422/55, 56, 57, 66, 422/67; 436/164, 166, 169, 170, 172

[56] References Cited

U.S. PATENT DOCUMENTS

| | | | |
|---|---|---|---|
| 3,847,553 | 11/1974 | Verbeck | 422/56 |
| 4,312,834 | 1/1982 | Vogel et al. | 422/56 |
| 4,430,299 | 2/1984 | Horne | 422/66 |
| 4,478,944 | 10/1984 | Gross et al. | 422/56 |

OTHER PUBLICATIONS

Butler, "J. Opt. Soc. Am." vol. 52, No. 3, pp. 292–299, 1962.
Renz et al., "Nucleic Acids Res.," vol. 12, No. 8 pp. 3435–3444, 1984.
Engvall, "Meth. Enzym.," vol. 70, Part A, pp. 419–439, 1979.
Collins et al., "Proc. Natl. Acad. Sci., U.S.A.," vol. 81, pp. 7683–7687, 1984.
Wickens et al., "Jour. Biol. Chem.," vol. 253, No. 7 pp. 2483–2495, 1978.
Nakane et al., "J. Histochem. Cytochem.," vol. 22, pp. 1084–1091, 1984.

*Primary Examiner*—Timothy M. McMahon
*Attorney, Agent, or Firm*—Joseph C. Schwalbach

[57] ABSTRACT

A light transmittance type analytical system for the rapid quantitation of minute amounts of an analyte in a fluid sample and an optical component and test device useful therein are; disclosed. The analytical system employs an assay in which the presence of the analyte in the assayed sample is productive of an insoluble substantially opaque, light absorptive colored end product. In the preferred use of the analytical system, the end product is formed in contact with a light and fluid permeable optical component in the form of a matrix of compacted substantially water insoluble granules of reflective material which has a light scattering coefficient of at least about 80 and is substantially nonabsorptive of light. Contact of particles of the end product with granules of the matrix causes a rapid and dramatic reduction in the light transmittance capability of the matrix which is monitored by the instrument to provide amplified quantitation of the analyte, which quantitation results from the two-fold effect of direct absorption of light by the end product, and reduction of the light scattering coefficient of the matrix granules caused by contact thereof by the end product. The instrument performs all of the steps of the assay when the test device is in operative position therein, and is well adapted for preprogrammed automated operation under computer control.

43 Claims, 7 Drawing Sheets

LIGHT TRANSMITTANCE TYPE ANALYTICAL SYSTEM AND VARIABLE TRANSMITTANCE OPTICAL COMPONENT AND TEST DEVICE FOR USE THEREIN

CROSS REFERENCE TO RELATED APPLICATION

This Application is a continuation in part of my application Ser. No. 07/559,252 filed on Jul. 30, 1990 which was a continuation in part of my application Ser. No. 07/069,960 filed Jul. 6, 1987. Both of these prior applications are now abandoned.

BACKGROUND OF THE INVENTION

1. Technical Field

This invention relates in general to the quantitive determination of minute amounts of substantially opaque insoluble colored light absorptive substances, and more particularly to a highly sensitive light transmittance type optical system useful in conjunction with analytical assays productive of such substances, for the rapid determination of the presence of minute amounts of such substances at levels which have heretofore been undetectable by the use of conventional techniques.

2. Background Art

Assays such as immunological assays and nucleic acid hybridization probe assays, have been the subject of much research and development activity in recent years. These and other assays have employed labelled entities which result in the production of a light absorptive colored end product as an indication of the presence of a particular analyte in a fluid specimen assayed.

In such assays it is common to bind to a portion of the analyte a reporter component having an enzymatic label capable of catalyzing the production of a colored light absorptive end product when contacted by a suitable substrate, and the quantity of the analyte in the specimen is usually determined by subjecting the colored end product to reflectance photometry or spectrophotometric light absorbence measurement.

Various formats have been developed for assay performance, and much effort has been expended to maximize the efficiency thereof in order to be able to quantitate lower and lower levels of analyte in a specimen. However, various probems have been encountered in such development.

In those assays in which the presence of a particular analyte in a specimen is indicated by the presence of a quantity of a soluble colored pigment in a clear solution, it is standard practice to measure the absorbence of the pigment spectrophotometrically as mentioned above. In this procedure, monochomatric light is directed through the solution of interest and toward a light detector such as a photodiode. The amount of the analyte is determined as a function of the amount of light absorbed by the colored pigment, as measured by the difference between the amount of incident monochromatic light and the amount of light reaching the light detector. More particularly, the amount of light absorbed is described by the Beer-Lambert Law which is often expressed as $$\text{Log} \frac{I_o}{T} = elC = A(\text{absorbence})$$

in which $I_o$ is the incident monochromatic light
$I$ is the transmitted light
$e$ is the molar extinction coefficient
$l$ is the length of the light path through the absorber, and
$C$ is the concentration of the absorber.

It will be observed that in the above equation the absorbence is proportional to the molar extinction coefficient, the length of the light path, and the concentration of the absorber. Thus, when measuring the concentration of an analyte in a liquid sample having a low molar extinction coefficient, or a sample having a very low concentration of analyte, the concentration is sometimes increased through evaporation of the sample and/or the sample is placed in a cuvette with a very long light path length. However, neither of these alternatives provides a practical solution in those instances where the sample, Without evaporation, has a volume too small to fill a standard cuvette.

As reported by Butler, W. L., in J. Opt. Soc. Am., Vol. 52, 292-299, (1962), one approach to the small sample problem involves the intensification of absorption by light scatter. In the reported procedure, various amounts of light scattering particles, e.g., particles of calcium carbonate, were added to a clear solution of soluble pigment. This introduced an additional factor into the absorbence equation above illucidated, so that $A = \beta elC$, wherein $\beta$ represents the increased light path length due to light scatter from the scattering particles. Butler found that the value for $\beta$ was as much as 100, indicating that light path length through the optical cell was 100 times longer than it was before the scattering particles were introduced into the solution. He also found that the absorbence of the sample in the light scattering mixture was substantially greater than that of the same amount of sample added to plain water. The magnitude of the increase is the value of $\beta$.

Current developments in nucleic acid hybridization assays, as well as immunological assays, include the detection of a conjugate of a labelled component with a component bound to a nitrocellulose filter. Such detection involves the measurement of the intensity of visibly colored areas on the filter as indicative of the amount of analyte in a test sample. One such procedure is reported by Renz et al in Nucleic Acids Res., Vol. 12, 3435-3444, (1894). In the reported procedure, nucleic acid probes labelled with peroxidase or alkaline phosphatase were annealed to nitrocellulose bound target nucleic acid. The presence of the substrate caused the label to produce a pigmentation on the paper, the intensity of which was read spectrophotometrically.

Certain immunological assays also involve similar procedures. In one such assay, a liquid specimen containing one component of an antibody/antigen couple, e.g., an antigenic analyte, is applied to a nitrocellulose membrane or the like having bound thereto a capture antibody specific for the analyte. This causes binding of the antigenic analyte to the capture antibody and thereby to the membrane. A solution containing a reporter component comprising an enzymatically labelled antibody to said antigenic analyte is run through or over the membrane to cause formation of a conjugate of said labelled antibody with the antigenic analyte. Any unbound labelled antibody is then removed from the membrane, as by washing, and a solution containing a substrate for the enzymatic antibody label is then run over or through the membrane to produce a pigmentation on the membrane indicative of the presence of the analyte in the specimen assayed. The pigmentation intensity is then read by reflectance spectrophotometry.

In order to achieve greater sensitivity in assays of the general type just described, it has become increasingly important to detect the presence of smaller and smaller quantities of a colored end product to thereby correspondingly detect smaller and smaller quantities of analyte in a test sample. However, there are a variety of problems associated with such assays, some of which are nonuniform color, chemical incompatability, poor membrane wetting, poor optical quality, and ineffective binding.

SUMMARY OF THE INVENTION

With the foregoing in mind, it is a general object of the present invention to provide improved light transmittance type optical system which is useful in conjunction with known analytical assays to provide quantitation of substantially opaque insoluble light absorptive substances or end products produced by such assays at levels not currently investigated because the amounts thereof produced are too small to be detectable by known techniques.

Another object of the invention is to provide an improved light transmittance type optical system which comprises a test device including at least one optical component in the form of a matrix of reflective substantially water insoluble granules which are substantially nonabsorptive of light and have interstices therebetween providing fluid passageways through the optical component.

Another object of the invention is to provide an improved light transmittance type optical system as aforedescribed which can provide quantitation of said substantially opaque insoluble colored end products as said end products are produced.

Still another object of the invention is to provide an optical system of the class described which is adapted to have particles of a substantially opaque light absorptive insoluble colored assay end product formed within the fluid passageways of its optical component, which particles contact granules exposed therein, there being means for monitoring the light transmittance capability of said optical component during formation of said end products; contact of particles of said end product with said component granules causing an unexpectedly large and rapid reduction in the light transmittance capability of said optical component, caused partly by the expected absorption of incident light by said end product and partly by an unexpected reduction in the light scattering coefficient of the granules contacted by particles of said end product, the reduction in light transmittance capability of said optical component being proportional to the amount of said end product in contact with said granules.

A still further object of the invention is to provide a test device including a carrier formed with at least one well in which said optical component is accommodated, said carrier having channel means in communication with said at least one well and through which fluid can pass to and through the fluid flow passage means of said optical component in said well.

A further object of the invention is to provide an improved instrument for use with said test device, said instrument having means for causing flow of fluid through the channel means of the test device to and through the at least one optical component therein, said instrument also having means for subjecting said optical component to light transmittance measurement.

Other and further objects of the invention will become apparent to those skilled in the art as the description proceeds, reference being had to the accompanying drawings.

BRIEF DESCRIPTION OF THE DRAWINGS

In the drawings accompanying and forming a part of this application.

DESCRIPTION OF THE PREFERRED EMBODIMENT

Figure 1:
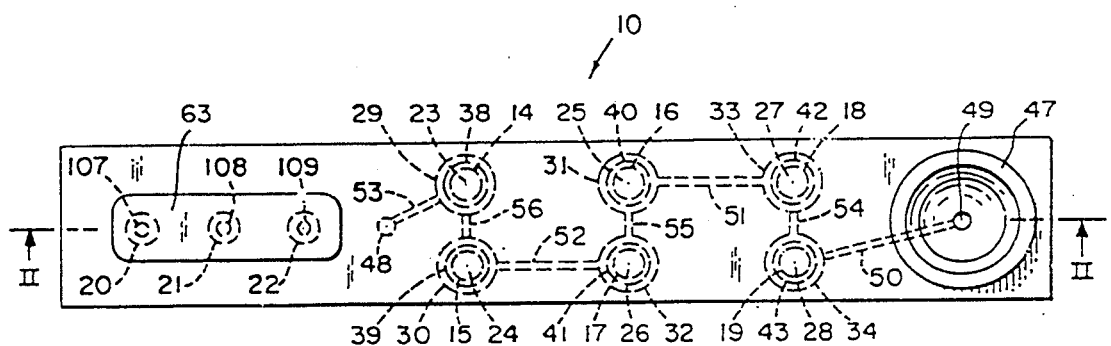
FIG. 1 is a plan view of the test device of the present invention.
Figure 2:
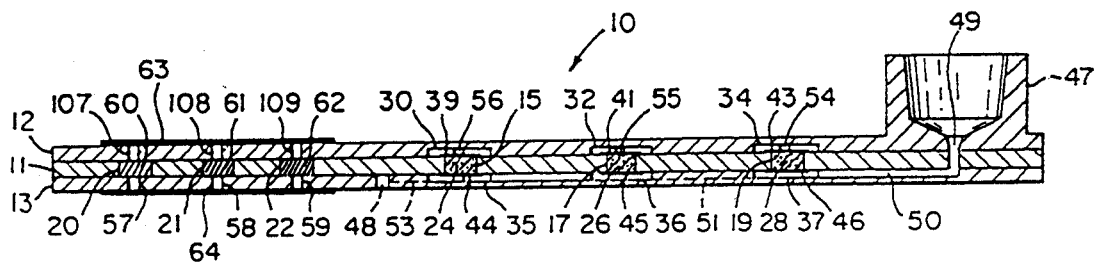
FIG. 2 is a vertical sectional view of the test device, in somewhat enlarged vertical dimension, taken generally along the line II—II of FIG. 1.

Referring now to FIGS. 1 and 2 of the drawing, the numeral 10 indicates an elongated rectangular multiple assay test device which, in the illustrated embodiment, has a thickness substantially less that the width thereof. As shown in FIG. 2, the test device comprises a laminate of an intermediate layer 11, a top layer 12, and a bottom layer 13. The layers 12 and 13 may be made of any suitable transparent material, such as acrylic plastic, and the layer 11 may be made of any suitable opaque material such as black ABS plastic. The layers 11, 12 and 13 are bonded together by any suitable plastic adhesive.

Figure 4:
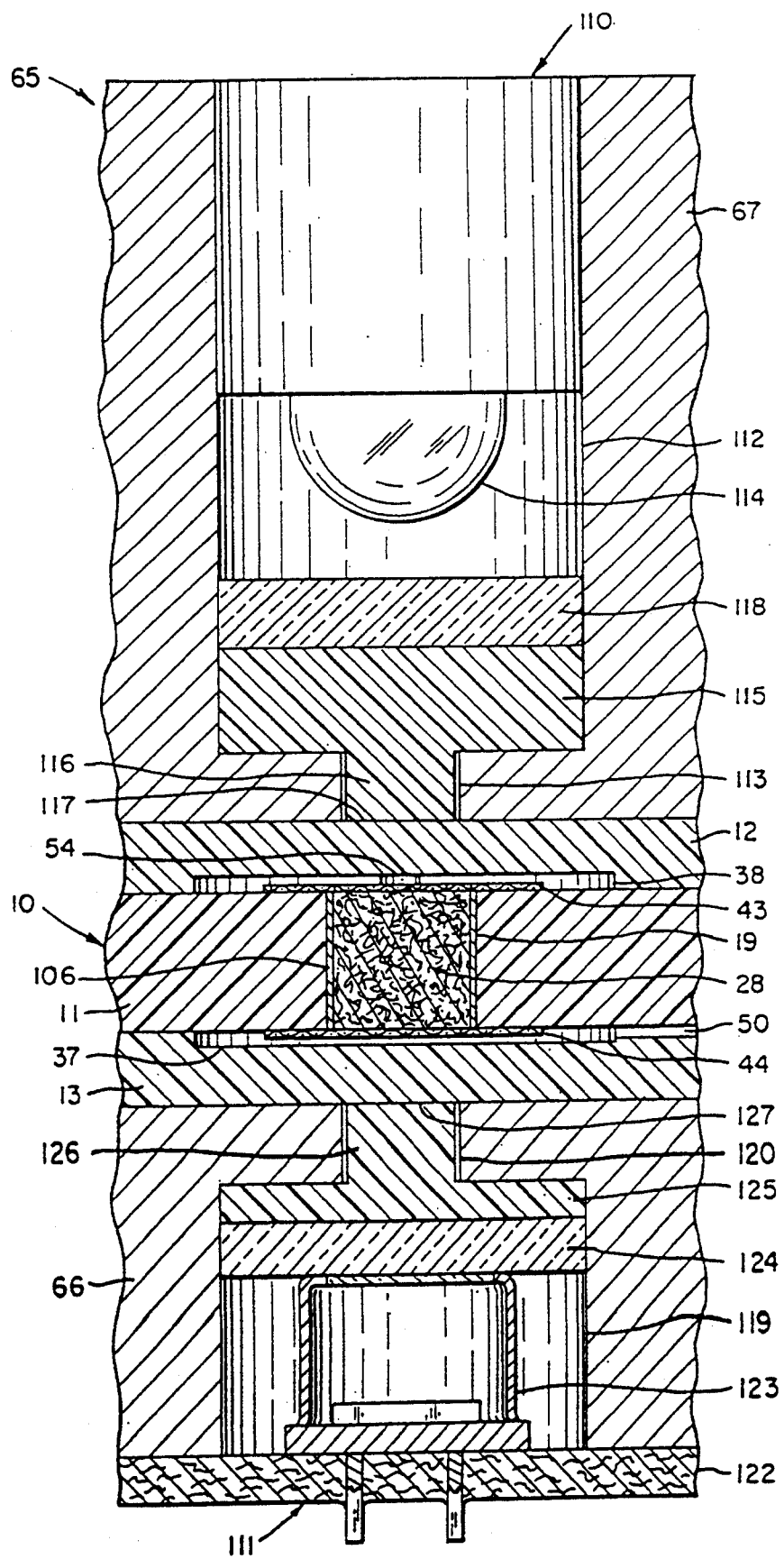
FIG. 4 is an enlarged partial vertical sectional view through a portion of the instrument and test device of FIG. 3 illustrating the relationship of one test device well and matrix with an associated optical assembly of the instrument.

The intermediate layer 11 of the illustrated test device is formed with a plurality of cylindrical bores or wells therethrough arranged in spaced parallel rows of three each and numbered respectively 14, 15, 16, 17, 18 and 19 as shown. Each of the bores or wells 14 to 19 is preferably lined with a tubular cylindrical liner which is substantially nontransmissive of light and has a highly reflective inner surface. One such liner, numbered 106, is illustrated in FIG. 4. Alternatively, the surfaces of the bores or wells 14 to 19 may be overlaid with a highly reflective surface of metallic or other suitable material. The liners 106 may be made of such metals as aluminum, stainless steel, chrome plated brass or the like. The intermediate layer 11 is also formed with three spaced aligned cylindrical bores or wells therethrough numbered respectively 20, 21, and 22 as shown.

Filling the wells 14 to 19, respectively, are optical components in the form matrices of compacted highly reflective granules, said matrices being numered 23, 24, 25, 26, 27 and 28, respectively. If desired, the tubular liners 106 can conveniently form molds within which the reflective granules are compacted, for example under a pressure of about 10 psi, to form the matrices 23 to 28. Alternatively, said matrices in tablet form can be inserted into the liners 106. Each of said matrices has exposed therein a different capture substance (not shown) which, as will appear hereinafter, is capable of binding thereto at least a portion of an analyte to be detected.

Figure 5:
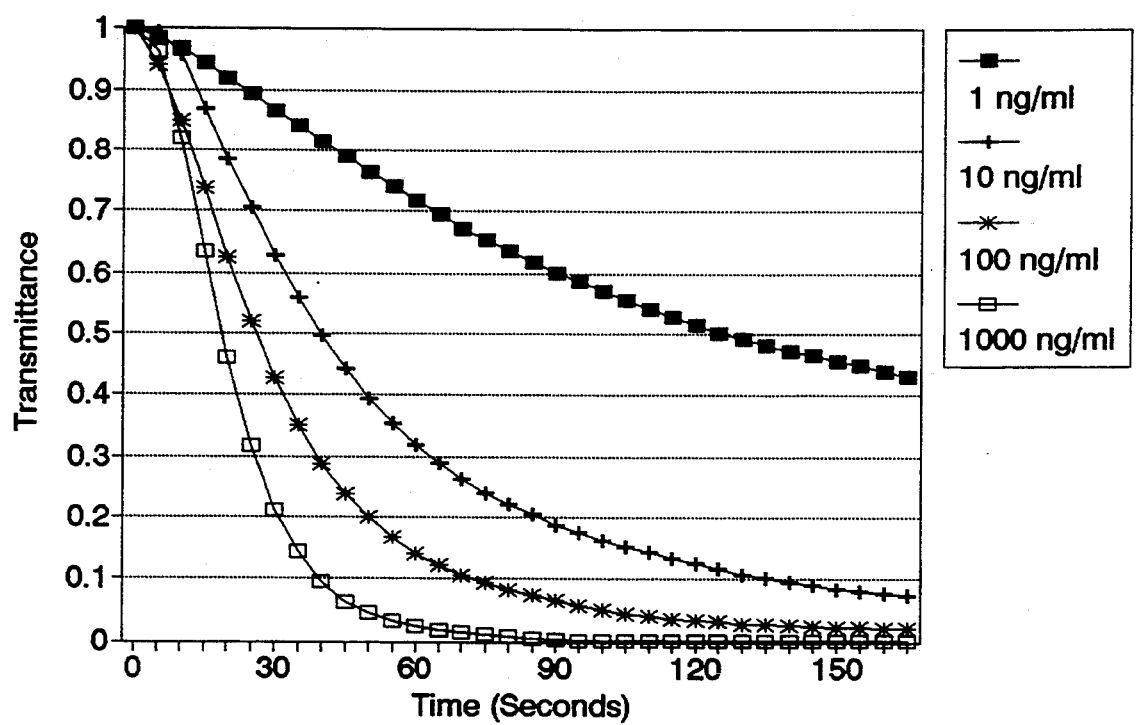
FIG. 5 shows a family of curves illustrating the changes in transmittance of matrices of the present invention versus the time of formation of particles of substantially opaque insoluble colored end product produced when liquid samples in which IgG is present in known concentrations of 1, 10, 100, and 1,000 nanograms per milliliter, respectively, are assayed.

The lower surface of the upper layer 12 is formed with shallow cylindrical recesses 29 to 34 which are coaxial with the wells 14 to 19, respectively. The upper surface of the lower layer 13 is formed with similar shallow cylinderical recesses coaxial with the wells 14 to 19, respectively, three of which are shown in FIG. 2 and are numbered 35, 36 and 37. The recesses 37 and 38 are also shown in FIGS. 4 and 5.

In the illustrated embodiment of the invention granule retaining means in the form of circular layers of light transmissive mesh, 38, 39, 40, 41 42 and 43 respectively overlay the upper ends of the wells 14 to 19 within the recesssses 29 to 34. These mesh layers are bonded, as by a suitable solvent bonding agent such as methylene chloride, to the upper surface of the intermediate layer 11 around the periphery of the upper ends of the associated wells 14 to 19. Identical granule retaining circular mesh layers overlay the lower ends of the wells 14 to 19 and are similarly bonded to the lower surface of the intermediate layer 11 around the periphery of the lower ends of said wells, respectively. Three such layers are shown in FIG. 2 associated with the lower ends of wells 15, 17 and 19, said layers being numbered 44, 45 and 46, respectively. The mesh layers 43 and 46 are also shown in FIG. 4.

The test device 10 is provided with a sample cup 47 projecting upwardly from one end of the upper layer 12 thereof. Spaced intermediate the wells 14, 15 and 22 the lower layer 13 is formed with a bore 48 therethrough as shown in FIG. 2, which bore serves as an exit port. A bore 49 extends from the bottom of the cup 47 through the layers 12 and 11 as shown in FIG. 2, and serves as an entry port.

The test device 10 is also formed with channel means providing a fluid flow path from the entry port 49 serially through the flow passage means of each of the matrices 23 to 28 and out of the exit port 48. To this end, the upper surface of the lower layer 13 is formed with a channel 50 connecting the inlet port 49 with the recess 37 at the lower end of the well 19 as best shown in FIG. 2. The upper surface of the lower layer 13 is also formed with a channel 51 providing communication between the recesses in layer at the lower ends of the wells 16 and 18 as best shown in FIG. 1. A channel 52 formed in the upper surface of the lower layer 13 provides communication between the recesses 35 and 36 at the lower ends of wells 15 and 17 as best shown in FIG. 2. A channel 53 formed in the upper surface of the lower layer 13 provides communication between the recess in layer 13 at the lower end of well 14 and the exit port 48, as shown in broken lines in both FIGS. 1 and 2. Channels 54, 55 and 56 formed in the lower surface of the upper layer 12 respectively provide communication between the recesses 33 and 34, 31 and 32, and 29 and 30.

The upper layer 12 is formed with bores therethrough numbered 107, 108 and 109, which bores are respectively coaxial with the wells or bores 20, 21 and 22. The lower layer 13 is formed with bores 57, 58 and 59 therethrough which are also respectively coaxial with the bores or wells 20, 21 and 22. The wells or bores 20, 21 and 22 are appropriately sized to accomodate premeasured amounts of dry, water soluble reagent means 60, 61 and 62, respectively, which will be described hereinafter. To protect the aforementioned reagent means from the effects of the environment until the test device 10 is to be used, an adhesive seal 63 closes the upper ends of the bores 107, 108 and 109 and is adhered to the upper surface of the upper layer 12. A similar seal 64 closes the lower ends of the bores 57, 58 and 59, and is adhered to the lower surface of the lower layer 13. The seals 63 and 64 are preferably made of pressure sensitive tape and, by virtue of their being readily peelable from the surfaces to which they are adhered, are totally removable to ready the test device 10 for use.

Figure 3:
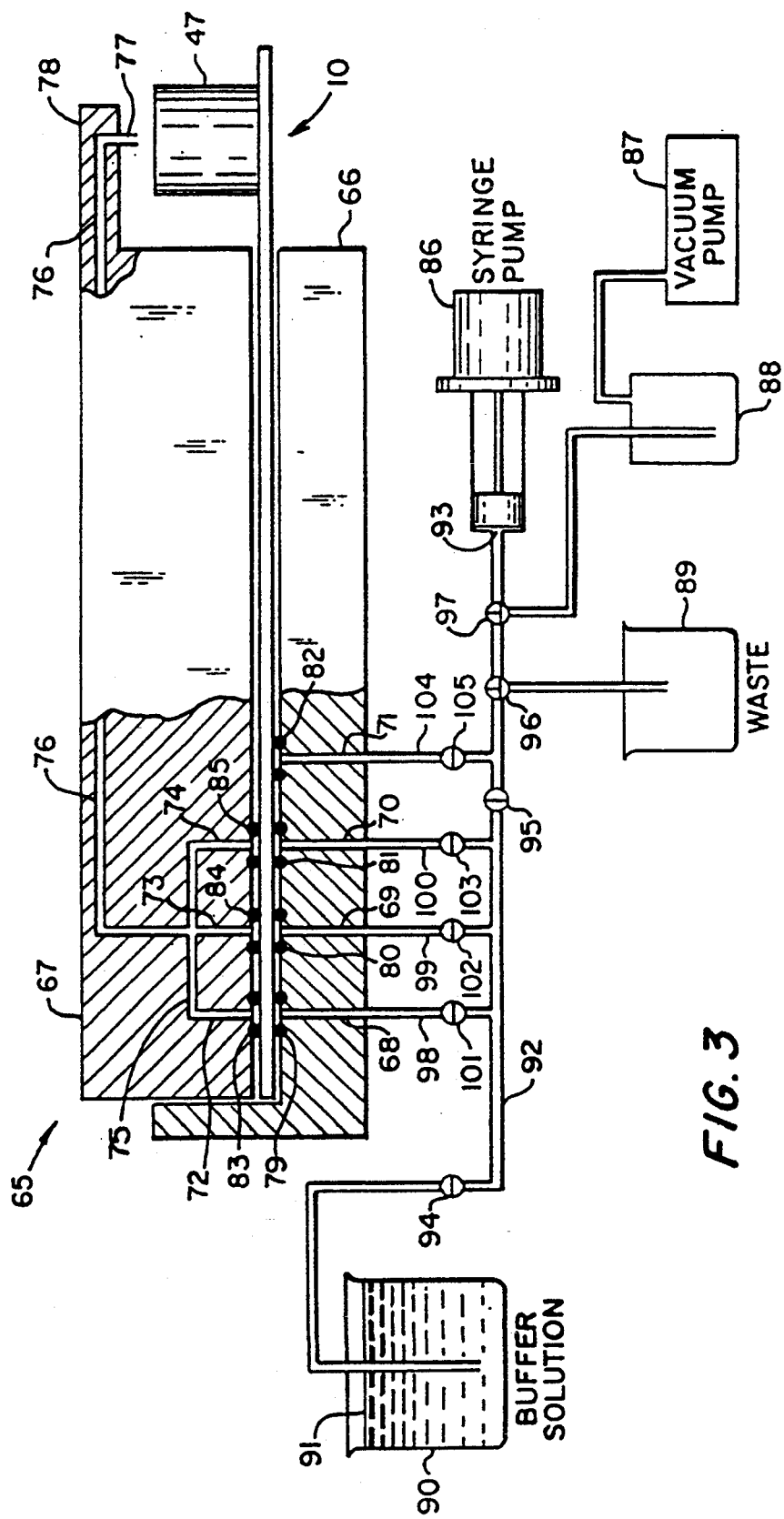
FIG. 3 is a semidiagrammatic side view, partially in vertical section, illustrating the test device in operative position within the instrument of the present invention, and showing the liquid handling system of the instrument.

Referring now to FIG. 3, the test device 10 is therein shown in operative position within an instrument 65 which comprises a base housing member 66 and a vertically movable upper housing member 67, both of which may be made of stainless steel. The housing members 66 and 67 provide housings for optical assemby units of the instrument 65, one of which units is shown in FIG. 4.

The base housing member 66 is formed with vertical bores 68, 69, 70 and 71 which are coaxially aligned with the test device bores 57, 58 and 59, and exit port 48, respectively, when the test device 10 is in the operative position shown in FIGS. 3 and 4. The upper housing member 67 is formed with vertical bores 72, 73 and 74 which are respectively coaxial with the bores 107, 108 and 109 of the test device 10 when the latter is in the operative position shown in FIGS. 3 and 4, there being a transverse bore 75 providing communication between the bores 72, 73 and 74 as shown. A horizontal bore or channel 76 provides communication between the upper end of the bore 73 and an outlet tube 77 which depends from a housing projection 78, preferably generally coaxially over the sample cup 47.

To provide a fluid-tight seal between the lower surface of the test device 10 and the upper surface of the housing member 66 overlaid thereby at the upper ends of the bores 68, 69, 70 and 71, the upper surface of the member 66 is formed with a circular groove of generally semicircular cross-section in spaced coaxial relation with each of the bores 69 to 71 as shown. Seated within the aforedescribed circular grooves are resilient O-rings 79, 80, 81 and 82 associated with the bores 68, 69, 70 and 71, respectively. To provide a similar sealing function, the upper housing member 67 is formed on its lower surface with circular grooves of semicircular cross-section in spaced coaxial relation with the lower ends of the bores 72, 73 and 74 to accomodate resilient O-rings 83, 84 and 85 respectively, as shown. The O-rings are preferably formed of suitable resilient material, such as silicone rubber.

As shown in FIG. 3, the instrument 65 is provided with a fluid flow control system which comprises a syringe type pump 86, a vacuum pump 87 provided with a liquid receptacle 88, a waste receptacle 89, and a reservoir 90 providing a container for a buffer or other suitable solution 91. A conduit 92 provides communication between the the lower portion of the interior of the reservoir 90 and the inlet/outlet opening 93 of the syringe pump 86, said conduit having one-way valves 94 and 95 therein, as well as three-way valves 96 and 97 disposed therein as shown. Conduits 98, 99 and 100 provide communication between the portion of the conduit 92 between valves 94 and 95 and bores 68, 69 and 70 of lower housing member 66, respectively, said conduits having one-way valves 101, 102 and 103 disposed therein as shown. A conduit 104, having a one-way valve 105 disposed therein, provides communication between the bore 71 of lower housing member 66 and the portion of the conduit 92 between the valves 95 and 96 as shown.

Referring now to FIG. 4, there is illustrated therein an optical assembly comprising a light source unit 110 carried by upper housing member 67 and a photodetector unit 111 carried by housing member 66 and aligned with the unit 110 as shown. While one optical assembly is illustrated in FIG. 4 as being in alignment with the matrix 28 in well 19 of the test device 10, it is understood that in the preferred embodiment of the instrument 65 there is one optical assembly in alignment with each of the wells 14 to 19 of the test device 10 when the latter is in the operative position shown in FIGS. 3 and 4.

As shown in FIG. 4, the upper housing member 67 is formed with a bore 112 and a reduced diameter counter bore 113 which extends to the lower surface of said member as shown. Mounted in the upper end of the bore 112 is light source means 114 which, in the preferred embodiment of the invention is an incandescent lamp, for example lamp No. L1007 sold by Gilway Technical Lamp, Inc., 272 New-Boston Park, Woburn, Mass. 01801. Disposed in the lower end of the bore 112 and in counter bore 113 is a cylindrical insert 115, for example of clear acrylic plastic. Insert 115 has a depending coaxial cylindrical projection 116 extending in coaxial spaced relation within the bore 113 and having a lower end surface 117 which is coplanar with the lower surface of the upper housing member 67 as shown. Disposed within the bore 112 in overlaying relationship with respect to the insert 115 is a cylindrical broad bandpass filter 118 preferably having a peak wavelength of 500 nanometers, and a half-peak bandpass of 240 nanometers. A suitable filter for this purpose is the glass filter BG38 available from Melles Griot, Irvine, Calif. 92670.

The lower housing unit 66 is formed with a bore 119 and a counter bore 120, the latter extending to the upper surface of the housing member 66 as shown. Overlaying the lower surface of the housing member 66 is a printed circuit board 122 which carries within the bore 119 a photodiode 123, such as the photodiode No. SD 080-12-12 available from Silicon Detector Corporation, 855 Lawrence Drive, Newbery Park, Calif. 91320-2288. A cylindrical broad bandpass filter 124 is disposed within the bore 119 above the photodiode 123 as shown, and it preferably has the same characteristics as the filter 118. A cylinderical plastic insert 125 overlays the filter 124 and has a coaxial cylindrical projection 126 extending in spaced coaxial relation within the counter bore 120 and having an upper end surface 127 coplanar with the upper surface of the lower housing member 66 as shown.

The insert 125, like insert 115, is preferably formed of acrylic plastic, which has an index of refraction of 1.5, as compared to an index of refraction of 1.0 for air. These inserts reduce the effective length of the light path between the light source means 114 and the photodiode 123, thereby increasing the efficiency of the optical assembly.

As will appear hereinafter, the instrument 65 incorporating optical assemblies including the incandescent light source 114 and filters 118 and 124, together with the optical components of test device 10, is well adapted for the taking of light transmittance measurements of the optical component or components. Instrument 65 is calibrated so that the output signal from each photodiode is directly related to the light transmittance of the matrix of test device 10 associated therewith.

Referring now to the optical components or matrices numbered 23 to 28, such matrices advantageously comprise dry compacted highly reflective granules (not shown) of material which is substantially water insoluble, has a light scattering coefficient of at least about 80, and a light absorption coefficient of substantially zero. The presently preferred materials for the granules are aluminum oxide and barium sulfate, both of which are almost 100% reflective of incident light. Aluminum oxide in the granule sizes suitable for use in the matrices 23 to 28 is generally available from commercial sources of grinding compounds, such as Micro Abrasives Corporation, P.O. Box 669, Westfield, Mass. 01086. Barium sulfate in granule sizes suitable for use in the matrices 23 to 28 is available as product No. 3758 from Sigma Chemical Co., P.O. Box 14508, St. Louis, Mo. 61378.

The granule size range is not narrowly critical, and the presently preferred range therefor is from about 5 microns to about 300 microns. The presently preferred granule size is about 35 microns. The granules in a given matrix are preferably of generally uniform size. The interstices between adjacent granules in matrices 23 to 28 provide fluid flow passageways permitting flow of a liquid sample as well as of liquid reagents through the respective matrices from one end to the other in a manner described hereinafter.

The layers of light transmissive mesh 38 to 43 which overlay the upper ends of the wells 14 to 19, respectively, and the corresponding mesh layers which overlay the lower ends of the wells 14 to 19 shown in FIGS. 1, 2 and 4, are preferably formed of 1 micron nylon mesh, for example Spectra/Mesh ® available from Spectrum Medical Industries, Inc., 60916 Terminal Annex, Los Angeles, Calif. 90054. Mesh of this size insures that the granules forming the matrices in the respective wells 14 to 19 are retained therein, said mesh at the same time permitting fluid flow through said wells and matrices.

The matrices 23 to 28 advantageously have a diameter range of from about 0.156 to about 0.203 inch, a diameter of about 0.187 inch being presently preferred. The thickness of the matrices 23 to 28 is preferably within the range of from about 0.020 inch to 0.125 inch, the presently preferred thickness being about 0.062 inch. It is understood, however, that these dimensions are not narrowly critical.

In one form of the invention carrier granules (not shown), for example granules of nitrocellulose, derivatized nylon or glass, are dispersed within at least some of the matrices 23 to 28. The carrier granules may be of generally the same size as the other highly reflective granules, and may be present in the matrices at a level of from about 1 to 25 percent of the volume of the respective matrices.

The aforementioned carrier granules preferably have bound thereto a capture substance capable of specifically binding an analyte of interest upon contact therewith. In the selected assay, when a liquid specimen containing such analyte is flowed through the fluid passageways of the matrix, the analyte is bound to the carrier granules by the capture substance. The thus bound analyte is then contacted with a substance capable of specifically binding thereto and which has bound thereto a chromogenic indicator or label capable of generating, within the matrix, particles of a substantially opaque.

The assays productive of particles of substantially opaque insoluble light absorptive colored indicator substance which can be performed within the matrices or optical components of test device 10 are many, and include, for example, nucleic acid hybridization probe assays and competitive and noncompetitive immunological assays. The assays preferred for use with the test device 10 are analogous to the well known sandwich filter binding nucleic acid hybridization probe assay and to the corresponding immunological assay of the sandwich type. For a thorough discussion of the methodology of enzyme immunoassays, reference is made to Engvall, E., Meth. Enzym., Vol. 70, part A, page 419, (1980), (Eds.) Vunakis, H. V. and Langone, J. J.

For a nucleic acid hybiridzation probe assay, prehybridized carrier granules having bound thereto unlabeled nucleic acid sequences complementary to target sequences in the respective analytes to be detected, are dispersed within the respective matrices 23 to 28 of test device 10. These sequences serve as capture probes, and upon passing through the matrix, a sample fluid to be assayed which contains target sequences from the analyte to be detected thereby, the target sequences hybridize with the capture probes and are bound thereto. Unbound sequences are then flushed from the matrix by a buffer solution passed through the matrix, leaving the target sequences bound to the capture probes. A solution of labeled nucleic acid sequences or probes complementary to the target sequences, but nonoverlapping with respect to any of the capture probe sequences, is then passed through the matrix, and the labeled probes therein hybridize with and are bound to the already bound target sequences. If desired, the labeled probes can be passed through the matrix at the same time that the target sequences are passed therethrough.

The labeled probes carry colorimetric labels, such as the enzyme horseradish peroxidase, which can be attached thereto by the procedure disclosed by Renz et al., supra. An alternative procedure which can be used is that disclosed by Jablonski, E. et al. in Nucleic Acids Research, Vol. 14, No 15, pages 6115 to 6128 (1986), in which procedure synthetic oligonucleotides are modified to covalently conjugate thereto, by means of a linker arm, an enzyme label such as alkaline phosphatase.

As the last step of the nucleic acid hybridization probe assay, a solution containing a substrate for the enzyme labels is then passed through the matrix to thereby produce at each label a small quantity or particle of a substantially opaque light absorptive, insoluble, end product. The matrix is then subjected to light transmittance measurement in the instrument 65, as described later herein, to thereby quantitate, in a highly sensitive manner, the amount of said end product formed in the assay. As the substantially opaque colored end product is formed within the matrix, the light transmittance capability of the matrix undergoes a rapid reduction over time. This is monitored by the instrument to produce a curve resembling those shown in FIG. 5. From the slope of that curve, the concentration of the analyte in the assayed sample can be determined, as will be described later herein, by a reference to a standard curve such as that shown in FIG. 6.

The nucleic acid sequences in the aforementioned capture probes and labeled probes can be produced by synthesis or by cloning. Synthesis of such sequences can be accomplished by the well known procedure involving the use of the sequencer instrument sold by Applied Biosystems, Inc., 850 Lincoln Center Drive, Foster City, Calif. 94404. Cloning of such sequences can be accomplished by the methods disclosed by Collins, P. L. et al, PNAS (USA), Vol. 81, pages 7683 to 7687 (1984); and Wickens, M. P. et al, Jour. Biol. Chemistry, Vol. 253, No. 7, pages 2483 to 2495 (1978).

The production of a matrix incorporating nitrocellulose carrier granules can be accomplished by the following procedure. A sheet of nitrocellulose paper (Schleicher and Schuell No. BA85) is dipped into a solution of capture probe sequences prepared either by cloning or by synthesis. Upon removal, the sheet is baked at a temperature of 70° C. for about 1,½ hours under a vacuum of less than 1 psi to covalently bond the capture probes thereto. The dried sheet is pulverized to granule sizes of from about 5 to about 300 microns, preferably 35 microns. The nitrocellulose carrier granules with capture probes bound thereto, are then placed in a column, and a prehybridizing solution is passed therethrough to block nonspecific binding sites thereon.

Prehybridizing solutions are well known in the art, and a satisfactory one for present purposes is a 50% vol/vol solution of formmide and water
0.05M sodium phosphate pH 7.0
0.8M sodium chloride
0.001M EDTA
0.05% (wt/vol) ficol
0.05% (wt/vol) bovine serum albumin
0.25% (wt/vol) salmon sperm DNA
0.05% (wt/vol) sodium dodecyl sulfate.

The prehybridized nitrocellulose carrier granules are then dried and are mixed with the selected other matrix granules, such as barium sulfate or aluminum oxide, in a ratio of from about 1 to about 25 percent of the volume of said latter granules. Compaction of this mixture under a pressure of about 10 psi produces a matrix in the form of a tablet which has the desirable fluid flow passageways therethrough aforementioned.

The matrices 23 to 28 of the test device 10 can alternatively incorporate derivatized nylon, nitrocellulose coated aluminum oxide, or glass carrier granules. The nylon granules can be produced by grinding to a granule size of from about 5 to about 300 microns, a sheet of GeneScreen TM or GeneScreenPlus TM hybridization transfer membrane made of derivatized nylon and available from New England Nuclear, 549 Albany Street, Boston, Mass. 02118. Glass granules useful as carrier granules in the matrices are available in the form of a ground glass slurry under the trademark Glassmilk ™ from BIO 101 Inc., P.O. Box 2284, La Jolla, Calif. 92038.

The derivatized nylon, nitrocellulose coated aluminum oxide or glass granules, as the case may be, are placed in a column, and attachment of capture probes thereto, prehybridization, drying, mixing with the other matrix granules, and compaction is carried out as described above with respect to nitrocellulose carrier granules to produce a finished matrix permeable to fluid flow therethrough.

When the assay productive of particles of substantially opaque insoluble colored indicator is an immunological assay, one or more of the matrices 23 to 28 in which such assay is to be carried out, can be prepared by binding capture antibodies reactive to a selected analyte, e.g., an antigen, to carrier granules of nitrocellulose, nitrocellulose coated aluminum oxide, derivatized nylon or glass having a size of from about 5 to about 100 microns. This is accomplished by placement of the selected granules in a column and passing therethrough a solution of capture antibodies. The selected antibodies used as the capture antibodies, as well as the antibodies used in the reporter antibodies as noted hereinafter, can be purchased from Antibodies, Inc., P.O. Box 1560, Davis, Calif. 95617. The remaining sites on the carrier granule surfaces are then blocked by passing therethrough a standard blocking solution containing a mixture of ionic and nonionic detergents such as sodium dodecyl sulfate and NP-40, a buffer such as Tris.HCl, and free protein such as bovine serum albumin, ovalbumin, or the like. Following the blocking step, the blocked carrier granules, with the capture antibodies bound thereto, are dried and mixed with the other selected matrix granules at a level of from about 1 to about 25 percent of the volume of the latter, and the mixture is used to form compacted matrices having fluid flow passageways therethrough in the manner previously described.

In use of a test device 10 having one or more matrices 23 and 28 appropriate for immunological assay purposes, a sample solution prepared as hereinafter described from a fluid specimen containing a specific analyte to be detected matrix. This causes the antigens in the sample solution to complex with the capture antibodies on the carrier particles and to be bound thereto. A buffer solution is then passed through the matrix to remove unbound sample constituents, and then a solution of reporter group-labeled antibodies is passed through the matrix. The reporter antibodies bind to the antigen to thereby form a sandwich of the capture antibodies, antigen and labeled antibodies. Enzymatic colorimetric labels can be attached to the antibodies by the procedure disclosed by Nakane, P. K. et al, J. Histochem Cytochem., Vol. 22, page 1084 (1984) or by Avrameas, S. et al, Scand. J. Immunol., Vol. 8, Suppl. 7, page 7 (1979).

Antibodies having enzyme labels bound thereto, and substrates therefor productive of particles of insoluble substantially opaque colored end product, are also commercially available. Examples of these are Human IgG with peroxidase label which is available from Sigma Chemical Co., as Catalog No. A0293; a substrate for peroxidase is 4-chloro-1-naphthol available as Sigma Catalog No. C6788 which produces an insoluble blue product; or 3,3 diaminobenzidine tetrahydrochloride as Sigma No. D5905 which produces an insoluble brown end product. Beta galactosidase is another enzyme label which catalyzes the production by its substrate of a colored insoluble end product. Any suitable labels may be used with the present invention.

The procedure for inducing color formation at the colorimetric labels, and monitoring measurement of the rapid change in light transmittance from the matrix produced during such color formation, provide a means for rapid and highly sensitive detection of the particles of substantially opaque insoluble end product of said assay and thereby of the level of analyte in the sample assayed, and will be described in detail hereinafter.

Referring again to FIGS. 1 and 2, the test device 10 comprises the reagent means 60, 61 and 62 which are selected for their usefulness in the particular assays to be carried out in the matrices of the test device. The test device 10 may comprise matrices 23 to 28 and reagent means which are respectively useful for the performance of nucleic acid hybridization probe assays for the detection of different specific target nucleic acid sequences in, for example, particular bacterial or viral pathogens or particular antibiotic resistance genes in a given specimen.

The test device 10 may alternatively comprise three sets of two matrices each, such sets being composed, for example, of matrices 23 and 24, 25 and 26, and 27 and 28, respectively. The capture probes on the carrier granules of one matrix of each set, for example, the matrices numbered 23, 25 and 27, each may have a nucleic acid sequence complementary to a first portion of a target nucleic acid sequence in a different particular bacterial or viral pathogen. The capture probes on the carrier granules of the other matrix in each set, for example those numbered 24, 26 and 28, may have a nucleic acid sequence complementary to a first portion of a nucleic acid sequence of an antibiotic resistance gene within the pathogen target nucleic acid sequence with which the corresponding probe of the same set is complementary. Such gene is one which confers to the pathogen, resistance to the use of a particular antibiotic in the treatment of a diseased state induced by such pathogen.

Examples of pathogen target sequences for which the capture probes can be specific, are those of *E. coli, klebsiella pneumonia, Pseudomonas aeruginosa, Staphylococcus aureus,* and *Haemophilius influenza*. The capture probes may also be derived, for example, from genes which respectively confer resistance to the antibiotics amoxicillin, ampicillin, and erythomycin, penicillin, and tetracycline. it is understood, of course, that the test device 10 can be provided with additional sets of matrices having capture probes complementary to a first portion of target sequences of other pathogens and/or other resistance genes, if desired.

The reagent means 62 in the well or bore 22 may comprise a water soluble reagent composition in solid form which is useful in the preparation of an aqueous hybridization medium, as will hereafter appear. The reagent means 62 also may comprise a plurality of different colorimetric enzyme labeled single-stranded nucleic acid probes which are complementary, respectively, to the second portions of the pathogen or gene target sequences with which the probes bound to the carrier granules in matrices 23 to 28 are complementary. If test device 10 is of the configuration in which the capture probes in the matrices 23, 25 and 27 each have a nucleic acid sequence complementary to a first portion of a target sequence in a bacterial or viral pathogen, and those in the matrices 24, 26 and 28 each have a nucleic acid sequence complementary to a first portion of the target sequence of an antibiotic resistance gene, the reagent means 62 comprises a plurality of different colorimetric enzyme labeled single-stranded nucleic acid probes respectively complementary to second portions of the aforementioned pathogen and gene target sequences. It is understood, of course, that the first and second portions of the aforementioned pathogen and gene target sequences do not overlap.

Thus, the reagent means 62 comprises reporter group-labeled probes which are respectively hybridizable with the same target sequences as the capture probes bound to the carrier particles in matrices 23 to 28. The reporter groups with which the probes of the reagent means 62 are labeled preferably comprise the enzyme horseradish peroxidase which, when contacted by a substrate therefor, catalyzes the production from the substrate of light absorptive particles of an intensely colored substantially opaque end product.

In addition to the plurality of reporter group-labeled probes, the reagent means 62 comprises reagent for the preparation of an appropriate amount, for example 20 ml, of a hybridizing medium which is produced by dissolving the reagent means 62 in a 50% (vol./vol) formamide and water buffer solution drawn from the reservoir 90 (FIG. 6) in a manner which will be described hereinafter. The table below sets forth the weight of each constituent of the reagent means 62 necessary to produce, at proper concentrations, 20 ml of hybridization medium, as well as the concentration of each of such constituents in the desired final hybridization solution.

TABLE 1

| Constituent | Weight of Constituent in Composition 39 | Concentration of Constituent in Final Hybridization Medium |
|---|---|---|
| sodium phosphate (mixture of mono and dibasic salt which produces pH 7.0) | .27 gm | 0.5M |
| sodium chloride | .93 gm | .8M |
| EDTA | 5.40 gm | 0.001M |
| ficol | .01 gm | 0.05% (wt/vol) |
| bovine serum albumin | .01 gm | 0.05% (wt/vol) |
| salmon sperm DNA | .05 gm | 0.25% (wt/vol) |
| sodium dodecyl phosphate | .01 gm | 0.05% (wt/vol) |
| reporter group-labeled probes | 20 mcg of each probe | 1 mcg of each probe/ml of hybridization medium |
| dextran sulfate | 0.01 gm | 0.5% (wt/vol) |

When the assays to be performed by the use of the test device 10 are immunological assays, the reagent means 62 takes the form of a water soluble reagent composition which preferably contains a plurality of enzyme labeled reporter antibodies specific, respectively, to the selected specimen analytes, i.e., target antigens, for which the capture antibodies matrices 23 to 28 are specific. The amount of a given antibody in reagent means 62 is determined empirically from the titer and association properties of the antibody, the procedure therefor being well known to those skilled in the art.

The labeled antibodies in the reagent means 62 take the form of the dried residue of commercially available solutions of ammonium or sodium salts of immunoglobulin (example IgG) fractions, to the antibodies of which enzymatic colorimetric labels have been attached following the procedure of Nakane et al or Avrameas et al, both supra.

The antigens for which the capture antibodies and reporter antibodies of reagent means 62 are specific may include human or animal viruses, bacteria, biological hormones, or response modifiers. Examples of human virus are human respiratory syncytial virus and HTLA III (AIDS) virus; examples of bacteria are S. aureus and H. influenza; an example of a biological hormone is human chorionic gonadotropin (hcG); and an example of a response modifier is tetrahydrocannabinol (THC).

The reagent means 61, in the form of test device 10 useful for nucleic acid hybridization probe assays, comprises a composition which is necessary to produce, for example, 20 ml of an aqueous buffer solution when dissolved in 50% (vol./vol.) solution of formamide and water drawn from the reservoir 90. The constituents of reagent means 61, the weight thereof and the concentration of the constituents in the final buffer solution are as follows:

TABLE 2

| Constituent | Weight of Constituent in Composition 40 | Concentration of Constituents in Final Buffer Solution |
|---|---|---|
| sodium chloride | 0.017 gm | 0.015M |
| sodium citrate (dry at pH7) | 0.006 gm | 0.0015M |

The reagent means 61 in the form of test device 10 useful for immunological assays differs from reagent means 61 in the test device 10 useful for nucleic acid hybridization probe assays. It comprises a sufficient weight of dry sodium dodecyl sulfate to form, for example, 20 ml of a 0.1% solution (wt./vol.) when dissolved in an appropriate amount of phosphate buffered solution containing 1% NP-40 detergent drawn from the reservoir 90.

The reagent means 60 is used in test devices 10 in which reporter probes or reporter antibodies are labeled with colorimetric enzymes, and it comprises a substrate for such enzyme labels. In test devices 10 useful for nucleic acid hybridization probe assays, as well as in test devices 10 useful for immunological assays, reagent means 60 comprises the substrate in water soluble, dry solid form. The presently preferred substrate is the substrate for horseradish peroxidase, i.e., diamino benzidine (DAB). The amount of DAB in reagent means 60 is sufficient to produce, for example, 20 ml of a 0.005% (wt./vol.) solution thereof when dissolved in either a 50% (vol/.vol.) solution of formamide and water, or phosphate buffered saline solution containing 1% NP-40 detergent.

The sample to be assayed by means of a nucleic acid hybridization probe assay may be one of a number of body fluids taken from a mammalian host, such as a specimen taken from the throat, nose or ear, or it may be a specimen of urine, blood or feces. The preparation from such specimen of a sample solution for use in such assay is as follows.

The body fluid specimen, for example, a 0.5 to 0.3 ml throat swab specimen, is suspended in about 10 ml of a denaturant medium which preferably takes the form of a 50% solution of guanidine thiocyanate. This releases nucleic acid fractions of any-bacterial or viral pathogens in the specimen. The released fractions may be either or both of RNA (single-stranded) and DNA (double-stranded). The denaturant medium, with the released nucleic acid fractions therein, is diluted 1 to 20 with water and is then applied to a minature ion exchange column, for example the column marketed under the trademark NACS ® by Bethesda Research Laboratories, Bethesda, Md. The released nucleic acid fractions bind to the ion exchange column, whereas the denaturant medium containing the remaining portions of the specimen, passes therethrough.

The nucleic acid fractions are then eluted from the ion exchange column using 0.1 to 0.3 ml of a mixture of 1M sodium chloride and 0.002M tris.HCl, pH 7.5. To one half of the volume of the eluent is added 1/20th volume of 10M sodium hydroxide, and the resulting solution is allowed to stand at room temperature for 5 minutes, after which 1/20th volume of 1M tris.HCl is added to neutralize. This results in the conversion to single-stranded form of any double stranded DNA fractions in the thus treated half volume of eluent. The other half volume of the eluent is then combined with the thus treated first half volume to provide 0.15 to 0.4 ml of a sample solution which contains, in single-stranded form, representative portions of any RNA and DNA contained in the specimen.

When an immunological assay of a body fluid specimen for the presence therein of bacterial or viral pathogens is to be performed using an appropriate test device 10, a sample solution for use in the test device is prepared by treating the specimen with an aqueous solution of lysozyme and bringing the resulting solution to a concentration of 1.0% sodium dodecyl sulfate This solution is then diluted with water containing NP-40 detergent to provide a final aqueous sample solution having therein a concentration of 0.1% dodecyl sulfate and 0.1% of NP-40.

In practice of the present invention utilizing the test device 10 and the instrument 65, the particular test device 10 is selected in accordance with the type of assay to be carried out, and the solution 91 in reservoir 90 is appropriate for the particular type of assay to be performed. For nucleic acid hybridization probe assays the buffer Solution 91 used in reservoir 90 is a 50% (vol./vol.) solution of formamide and water. For immunological assays the buffer 91 used in reservoir 90 is phosphate buffered saline solution containing 1% NP-40 detergent.

Assuming that a nucleic acid hybridization probe assay is to be performed, the selected test device 10 is placed in the instrument 65 and clamped between the housings 66 and 67 thereof as shown in FIG. 3 so that the O-rings 79 and 85 are in sealing engagement therewith. A previously prepared sample solution containing any single-stranded nucleic acid target sequences or fractions obtained from the specimen to be assayed is then placed in the sample cup 47. The assay is then performed instrumentally as follows.

With the valves of the instrument 65 in the initial positions shown in FIG. 3, the valves 94 and 95 are opened and the plunger of the syringe pump 86 is retracted to draw thereinto from reservoir 90 through conduit 92 a predetermined charge of buffer solution 91. The valve 94 is then closed and the valve 103 opened, after which the plunger of the syringe pump 86 is advanced a sufficient amount to pump buffer solution through conduit 100 and through reagent means 62 (FIG. 2). Reagent means 62 comprises hybridization reagent and reporter probes. The pump plunger is then reciprocated through a limited range to cause the buffer solution to be pumped back and forth through reagent means 62 for accelerated dissolution thereof. Upon dissolution of reagent means 62, the resulting hybridization solution containing reporter probes is then pumped through the channels 74 and 76 by fully advancing the syringe plunger to thereby discharge said solution from the outlet tube 77 into the sample cup 47 where it is mixed with the sample solution earlier placed therein.

The valves 95 and 103 are then closed, and the valve 105 is opened to provide communication between the syringe pump 86 and the exit port 48 of the test device 10 shown in FIGS. 1 and 2. The plunger of the syringe pump 86 is then retracted to cause the mixed solution in the sample cup 47 to be drawn from the cup 47 serially through the fluid flow passageways of all of the matrices 23 to 28. The plunger of syringe pump 86 is preferably reciprocated a number of times to cause the solution from the cup 47 to be pumped back and forth through the fluid flow passageways of matrices 23 to 28, after which the plunger is completely retracted to withdraw the solution from the matrices thereinto. The valve 105 is then closed and the valve 96 rotated clockwise 90, after which the syringe pump plunger is fully advanced to discharge the solution therein into the waste receptacle 89.

At this stage, any target sequences which were in the sample solution have become hybridized to the capture probes on the carrier granules of the matrices 23 to 28 complementary therewith, and the labeled probes in said solution have also hybridized to such target sequences. The valve 96 is then returned to the position of FIG. 3, and with valves 94 and 95 opened, the plunger of the syringe pump 86 is retracted to withdraw thereinto another charge of buffer solution 91 from reservoir 90. The valve 94 is closed and valve 102 is opened, and the plunger of syringe pump 86 is advanced to pump the charge of buffer solution 91 to and through the reagent means 61, the plunger being reciprocated through a limited range to pump solution 91 back and forth through the reagent means 61 to dissolve the same and thereby produce a buffer wash solution.

The plunger of syringe pump 86 is then retracted to draw the thus made wash solution thereinto, after which the valves 95 and 102 are closed and the valve 105 is opened. The syringe pump plunger is then advanced to force the buffer solution through the conduit 104 and serially through the fluid flow passageways of all of the matrices 23 to 28, said plunger being reciprocated to pump said solution back and forth through said matrices to remove any unbound nucleic acid target sequences or fractions and any unbound labeled probes from said matrices. The syringe pump plunger is then fully retracted to withdraw the wash solution from the matrices, and valve 105 is closed. Valve 96 is then rotated clockwise 90 from its position in FIG. 3, and the syringe pump plunger is fully advanced to discharge the wash solution into the waste container 89.

With the valves of the instrument 65 disposed as shown in FIG. 3, except that valves 94 and 95 are opened, the plunger of syringe pump 86 is retracted to withdraw thereinto another charge of buffer solution 91 from reservoir 90. Valve 94 is then closed and valve 101 opened, and the syringe pump plunger is advanced to pump the buffer solution to and through the reagent means 60, said plunger being reciprocated to cause the buffer solution to be pumped back and forth through the reagent means 60 to dissolve the same and provide a solution of enzyme substrate. The syringe pump plunger is then fully retracted to withdraw the enzyme substrate solution thereinto, after which the valve 95 is closed and valve 105 is opened.

At this stage the lamps in registry with each matrix, such as the lamp 114 shown in FIG. 4 as being in registry with the matrix 28, are switched on to subject each associated matrix to intense illumination. Because of the optical characteristics of the granules in each matrix, substantially all of the incident light is transmitted through each matrix and is sensed by the associated photodiode, such as the photodiode 123 shown in FIG. 4.

The circuitry on the printed circuit board 122 records the output of the respective photodiodes at one second intervals when the matrices are illuminated. The initial photodiode output reading corresponds to 100 percent transmittance, and any lesser reading is recorded as a percentage of the intial reading and as a corresponding percentage of the initial 100 percent transmittance value.

The syringe pump plunger is then advanced to pump the substrate solution through the conduit 104 and serially through the fluid flow passageways of all of the matrices 23 to 28 at a rate, for example, of 2 milliliters per minute. Again, the syringe pump plunger can be reciprocated to cause the substrate solution to be pumped back and forth through the matrices for maximum contact with the enzyme labels. During this time the instrument monitors the output of all of the photodiodes and records on a second-by-second basis the percentage transmittance from the respective matrices.

In each case where a target sequence had hybridized to a capture probe and an enzyme labeled probe had hybridized to a bound target sequence within a matrix, the flow of substrate solution back and forth through that matrix causes the enzyme label to catalyze the formation of small particles of an insoluble substantially opaque light absorptive colored end product in the matrix which particles come to rest generally offset downstream from the site of the respective catalyzing enzyme molecules.

The increasing amount of insoluble light absorptive end product formed over time has an immediate and dramatic effect on the transmittance from the respective matrices. More specifically, as they are formed over time, the particles of end product reduce the transmittance by directly absorbing a portion of the incident light. In addition, however, such colored end product particles, being substantially opaque overlay surface portions of the matrix granules contacted thereby with a masking action which prevents light flow in either direction through such granule surface portions. This substantially reduces the ability of the contacted matrix granules to scatter light, i.e., it substantially reduces the light scattering coefficient of said granules, to thereby compound the reduction in transmittance caused by the aforementioned light absorption.

As a result, the photodiode associated with such affected matrix senses a rapid reduction in percent transmission, initially with a steep generally straight line slope which, with time, tapers off to a more gentle slope. When this point is reached, the lamps are extinguished, and transmittance monitoring is stopped.

If the amount of amount of colored end product by the assay is smaller than may be detectable by the procedure described, a more sensitive detection may be made by continuing the irradiation and the pumping of substrate for a predetermined total time period, such as 10 minutes, for example. At that point the pumping of substrate is stopped and the light shut off. The syringe pump plunger is then fully retracted to withdraw the substrate solution thereinto, after which the valve 105 is closed and valve 96 is rotated clockwise 90° from its position in FIG. 3. The syringe pump plunger is then fully advanced to discharge the substrate solution into the waste container 89. The valve 105 is then opened, valve 96 is rotated back to its position of FIG. 3, and valve 97 is rotated counterclockwise 90° from its position in FIG. 3. This causes a vacuum from pump 87 to draw air in through the cup 47 and through the fluid flow passageways of all of the matrices 23 to 28, the moving air carrying with it any liquid with which it comes in contact, discharging said liquid into the receptacle 88.

The light 114 and its counterparts are then switched on, and a reading of the light transmittance from the dried matrices is then made. Drying of the matrices provides amplification of the light path length therethrough to thereby provide amplified transmittance readings which may indicate the presence in the matrices of even minute amounts of colored end product not detectable when the matrices were wet. In either case, the amount of colored end product produced by an assay and detected by the invention is precisely related to the amount of analyte, i.e., bacterial or viral pathogens present in the specimen from which the sample solution assayed was derived.

In order to perform immunological assays with the test device 10 and instrument 65, the capture antibodies bound to the carrier granules or to a nitrocellulose film coating the granules, as the case may be, in the matrices 23 to 28 thereof are selected for their specificity for the particular antigens for which the specimen is to be assayed. The test device 10 is then placed in the instrument 65 as shown in FIG. 3, and the buffer solution 91 in the reservoir 90 is a standard phosphate buffered saline containing 1% NP-40 detergent. The specimen to be assayed is processed in the manner described earlier herein, and the resulting sample solution is placed in the sample cup 47.

With all of the valves of the instrument in the positions shown in FIG. 3, with the exception that valve 105 is opened, the plunger of the syringe pump 86 is retracted to draw the sample solution from the cup 47 serially through the fluid flow passageways of all of the matrices 23 to 28, the plunger being reciprocated to pump the solution back and forth through the matrices to insure maximum contact of any antigens therein with the capture antibodies bound to the carrier particles or to the nitrocellulose film in said matrices.

Such contact results in complexing of the antigens in the sample solution with said capture antibodies specific therefor. The plunger of syringe pump 86 is then retracted to remove the solution from the matrices, after which the valve 105 is closed and valve 96 is rotated clockwise 90° from its position in FIG. 3. The syringe pump plunger is then advanced to discharge the sample solution and any unbound antigen therein into the waste receptacle 89.

The valve 96 is then returned to the position thereof shown in FIG. 3, and valves 94 and 95 are opened, after which the syringe pump plunger is retracted to withdraw a charge of buffer solution 91 from the reservoir 90. The valve 95 is then closed, and with the valve 105 opened, the plunger of syringe pump 86 is advanced to pump the charge of buffer solution serially through the fluid flow passageways of all of the matrices 23 to 28, the plunger being reciprocated to pump the solution back and forth through said matrices to wash therefrom unbound antigen and other sample constituents. The plunger of syringe pump 86 is then retracted to withdraw thereinto the wash solution from the matrices, after which the valve 105 is closed and valve 96 is rotated clockwise 90° from its position of FIG. 3. The plunger of syringe 86 is then advanced to discharge the wash solution to the waste container 89.

The valve 96 is then returned to its position of FIG. 3 and valves 94 and 95 are opened, after which the plunger of syringe pump 86 is retracted to withdraw another charge of the buffer solution 91 from the receptacle 90. Valve 94 is then closed and valve 103 opened, after which the plunger of the syringe pump 86 is advanced to pump the charge of buffer through the conduit 100 and the reagent means 62 containing the reporter antibodies. Reciprocation of the syringe pump plunger causes pumping of the buffer solution back and forth through the reagent means 62 to dissolve said reagent means and produce a reporter antibody solution therefrom. The plunger of the syringe pump 86 is then retracted to withdraw the reporter antibody solution thereinto.

Valve 103 is then closed and valve 105 is opened, after which the plunger of the syringe pump 86 is advanced to pump the reporter antibody solution serially through the fluid flow passageways of all of the matrices 23 to 28, the plunger being reciprocated to pump the reporter antibody solution back and forth through said matrices to ensure maximum contact of the reporter antibodies with the antigen bound to the capture antibodies on the carrier particles of said matrices. The reporter antibodies complex with the bound antigen on contact therewith and are thereby bound to the same carrier granules or film as said antigen, forming thereon a sandwich of capture antibody, antigen and reporter antibody.

The syringe pump plunger is then retracted to withdraw the spent reporter antibody solution thereinto from the matrices 23 to 28, after which valve 105 is closed and valve 96 is rotated clockwise 90° from its position in FIG. 3. The syringe pump plunger is then advanced to discharge the spent reporter antibody solution into the waste container 89.

Valve 96 is then returned to the position of FIG. 3, and valves 94 and 95 are reopened, after which the plunger of the syringe pump 86 is retracted to withdraw thereinto another charge of buffer solution 91 from the revervoir 90. Valve 94 is then closed and valve 102 opened, after which the syringe pump plunger is advanced to pump the buffer solution through the conduit 99 and through reagent means 61, the plunger being reciprocated for force the buffer solution back and forth through the reagent means 61 to dissolve the same. The resultant buffer wash solution has a concentration of 0.1% (wt./vol.) of sodium dodecyl sulfate, and the syringe pump plunger is then retracted to withdraw said solution thereinto.

The valves 95 and 102 are then closed and valve 105 is opened. The plunger of syringe pump 86 is then advanced to force the buffer wash solution through the conduit 104 and serially through the fluid flow passageways of all of the matrices 23 to 28, the plunger being reciprocated to cause the wash solution to flow back and forth through said matrices to better remove therefrom unbound reporter antibody. The syringe pump plunger is then retracted to withdraw thereinto the wash solution. Valve 105 is then closed and valve 96 is rotated clockwise 90° from its position in FIG. 3, after which the syringe pump plunger is advanced to discharge the wash solution therefrom into the waste container 89.

The valves of the instrument 65 are then placed in the positions shown in FIG. 3, except that valves 94 and 95 are opened, and the plunger of syringe pump 86 is retracted to withdraw thereinto another charge of buffer solution 91 from reservoir 90. Valve 94 is then closed, and valve 101 opened, after which the plunger of syringe pump 86 is advanced to pump the buffer solution through conduit 98 and through reagent means 60 containing substrates for the reporter antibody labels. The syringe pump plunger is reciprocated to pump the buffer solution back and forth through the reagent means 60 to thereby dissolve the same, after which the plunger is retracted to withdraw the resultant substrate solution thereinto.

The light 114 and its counterparts are then switched on and an initial transmittance reading is taken, after which valves 101 and 95 are closed and valve 105 is opened, and the syringe pump plunger is advanced to force the substrate solution through the conduit 104 and serially through the fluid flow passageways of all of the matrices 23 to 28 at a rate, for example, of 2 milliliters per minute. Transmittance readings are taken on a second-by-second basis to monitor the effect of the formation of any substantially opaque colored insoluble product in any of the matrices in the same manner as described earlier with respect to analysis of samples for target nucleic acid sequences. The plunger is reciprocated to pump the substrate solution back and forth through said matrices and ensure thorough contact of the substrate with the enzymatic label on the reporter antibodies bound to the particles in said matrices.

Such contact produces the formation of particles of substantially opaque insoluble intensely colored end product at each of the labels of the bound reporter antibodies.

If there is no substantial or only a slight reduction in transmittance after pumping of the substrate for a predetermined period of time, for example ten minutes this is indicative of the fact that a very small amount of the insoluble colored end product is formed by the assay, and, the matrices can be dried as follows. The plunger of syringe pump 86 is retracted to withdraw thereinto the substrate solution, after which the valves 95 and 101 are closed, valve 105 is opened, and valve 97 is rotated clockwise 90° from its position of FIG. 3. This causes a vacuum from pump 87 to draw air in through the cup 47 and through the fluid flow passageways of each of the matrices 23 to 28, carrying with it any liquid contacted thereby which is discharged into the receptacle 88. The thus dried matrices 23 to 28 are then subjected to light transmittance measurement in the same manner as the dried matrices of the test device 10 used in the nucleic acid hybridization probe assays.

The level of light transmittance at each of the matrices 23 to 28 is indicative of the amount of insoluble substantially opaque colored end product produced by the assay, and thereby of the level of the respective analytes in the specimen which is the subject of the assay. As mentioned earlier, the light transmittance measurement of the dried matrices provides a substantially amplified signal which is indicative of the presence of even minute amounts of colored end product not detectable when the matrices are wet. In either case, the amount of colored end product produced by an assay and detected by the present invention is precisely related to the amount of analyte, i.e., antigen, in the specimen from which the sample solution was derived.

In the performance of assays using a test device 10 in which the reporter probes or antibodies are labeled with colorimetric labels, the concentration of analyte in the sample can be determined in several ways. For example, after an initial light transmittance measurement, the substrate can be caused to flow through the fluid flow passageways of the matrices for a specific period of time, after which a second light transmittance measurement is made. The measured change in light transmittance of the respective matrices is proportional to the amounts of the insoluble colored light absorptive end product produced therein by the assay, which amounts are proportional to the amounts of the various analytes in the respective specimens.

The presently preferred method involves causing the substrate to flow through the fluid flow passageways of the matrices at a specific rate, for example about 2 milliliters per minute, during which time the light transmittance from the matrices is monitored. In this procedure the rate of change in transmittance per unit time is proportional to the amount of the various analytes in the specimen.

Performance of assays by means of the improved test device 10 and instrument 65 is productive of dramatically improved results compared to performance of similar assays utilizing the conventional filter binding assay format. Moreover, a number of the disadvantages of that format are obviated thereby. For example, the invention removes the problem of uneven color development common to assays done on nitrocellulose membranes. Such uneven color development is due to membrane surface irregularities and can cause significant errors.

In the present invention, even if the carrier granules or the capture probes or antibodies are not dispersed uniformly throughout the matrices, the integration of the multiplicity of reflections from one particle to the next creates an even distribution of light therethrough. Since the approximately 1/16" thickness of the matrices is about 50 times greater than that of the conventional nitrocellulose membrane, there is much greater probability of the capture probes or antibodies being contacted by the target sequences or antigens from the specimen, particularly when the sample is pumped back and forth through the fluid flow passageways of the matrices. For the same reason, there is a much greater likelihood of the enzyme substrate contacting the labels of reporter probes or antibodies, particularly when the enzyme substrate solution is pumped back and forth through the fluid flow passageways of the matrices to maximize the formation of particles of the substantially opaque insoluble colored end product. Thus, with the present invention, binding of the target sequences or antigens to the capture probes or antibodies occurs very rapidly, and the color development similarly occurs very rapidly. Moreover the color development is amplified dramatically over that produced when conventional membrane assay techniques are used, thereby imparting to the invention dramatically improved sensitivity.

Color development of conventional membrane assays is frequently at a very low level and is difficult to quantitate. Performing the same assays utilizing the present invention, the improved sensitivity makes possible the detection and quantitation of levels of colored end product, and thereby of analyte, which are not detectable by conventional methods. The reason for such improved performance is the dramatic and rapid a reduction in the light transmittance through the matrix which, for the dual reasons stated earlier herein, results from the formation therein of the insoluble colored end product.

The improved sensitivity provided by the matrix format as described herein, as compared with the membrane format, involving reflectance photometry, is illustrated by the following procedure which shows that by use of the matrix format it is possible to detect levels of substantially opaque light absorptive particles, such as carbon black, which are orders of magnitude lower in concentration than can be detected using conventional reflectance photometry techniques. In this procedure various specific quantities of light absorptive granules of carbon black were deposited from liquid suspensions thereof uniformly onto spaced apart 3/16" diameter circular areas on the surface of a derivatized nylon membrane. The amounts of the carbon particles in the various circular areas were respectively 10 mg, 1 mg, 100 mcg, 10 mcg and 1 mcg. Of these concentrations, those down to 10 mcg were visible to the naked eye. Therefore, only those concentrations down to 10 mcg are detectable by conventional reflectance photometry techniques.

Amounts of carbon particles identical with those deposited on the membrane were then mixed with barium sulfate particles to form cylindrical matrices respectively containing the amounts of carbon particles noted above. The matrices were 3/16" in diameter and 1/16" thick. With the instrument 65, the light transmittance of each of the matrices containing carbon granules was measured, and concentrations down to about 1 ng were detected in the matrices.

It is apparent from these results that, by using the matrix format, the invention is able to detect minute amounts, of substantially opaque light absorptive particles i.e., 1 ng, of carbon granules, in contrast to the 10 mcg minimum amount detectable visually and by conventional techniques. This shows that the invention can detect substantially opaque light absorptive particles which are present in a quantity which is one ten thousandth of the minimum quantity detectable by conventional reflective photometry techniques.

In a modified form of the invention, the matrices 23 to 28 of the test device 10 do not incorporate carrier granules which are different from the highly reflective granules. Rather, the capture probes or capture antibodies, as the case may be, are bound directly to certain of the highly reflective granules in the respective matrices. In this form of the invention, the highly reflective granules used in the matrices 23 to 28 may, for example, be formed of polystyrene, sometimes referred to as polystyrene latex, said granules having a size of from about 5 to about 300 microns. Polystyrene is available from Sigma Chemical Co., P.O. Box 14508, St. Louis, Mo. 63178.

Prior to the formation of such modifed matrices, the capture probes or capture antibodies can be bound to polystryene granules by the procedure disclosed by Smith, K. O. et al, Meth. Enzym., Vol. 70, Part A, pages 338 to 416, (1981), (eds.) Vunakis and Langone. Polystyrene granules having capture probes or antibodies bound thereto by this procedure are mixed with like polystyrene granules not having capture probes or antibodies attached thereto, the mixture being compacted to form matrices 23 to 28 each having fluid flow passageways therethrough. The volume of polystyrene granules having capture probes or antibodies bound thereto is preferably within the range of from about 1% to about 25% of the volume of the matrices in which they are incorporated.

In another alternative and the presently preferred form of the invention, the matrices 23 to 28 do not require mesh layers 38 to 43 and the corresponding mesh layers which overlay the lower ends of the wells 14 to 19, and they also do not have carrier granules dispersed therein. Rather, the highly reflective granules are each coated with a film of nitrocellulose or other material having similar properties.

One method for producing the alternative matrices is to dissolve about 100 milligrams of nitrocellulose filter material in about 30 milliliters of a suitable solvent, such as acetone, to thereby produce a clear colorless solution. To this solution is added about 30 grams of aluminum oxide granules preferably having a diameter of about 35 microns, to thereby produce a mixture having a plastic consistency resembling that of peanut butter.

A tubular cylindrical well liner, such as the liner 106 in FIG. 4, is placed on a firm flat surface and is filled with about 150 milligrams of the plastic aluminum oxide/nitrocellulose mixture. Using a glass microscope slide or similar flat surfaced instrument, the mixture is compressed firmly into the well liner, substantially completely filling the same.

The mixture is then allowed to dry in the uncovered liner. Evaporation of the acetone from the mixture is productive of a fluid permeable cylindrical rigid matrix or tablet of compressed, highly reflective granules each coated with a film of nitrocellose. The nitrocellulose coating rigidly binds together contacting granules, while providing fluid flow passage means through such matrices which present less resistance to fluid flow therethrough than the fluid flow passageways in the matrices described earlier herein.

A solution of an analyte capture substance, such as a capture antibody, is then caused to flow through the matrix. This results in the capture antibodies being bound to the nitrocellulose surface of the fluid flow passage means within the matrix granules. A bovine serum albumim standard blocking solution of the type referred to earlier herein is then caused to flow through the matrix to block the remaining sites on the surface portions of the nitrocellulose film exposed within the fluid passageways of the matrix, and the matrix is then ready for use.

The following examples demonstrate how the invention is utilized for the purpose of carrying out assays for the rapid determination of very minute quantities of analyte in a fluid sample. The first example describes a standard sandwich type noncompetitive immunoassay for the determination of the presence in a fluid sample of a minute amount of human IgG, a large molecular weight antibody. The second example describes a competitive type immunoassay for the determination of the presence in a fluid sample of a minute amount of T3, a small molecular weight hormone.

EXAMPLE 1

The procedure followed in this example utilized four test devices generally similar to the test device 10 shown in FIGS. 1 and 2, but which each had only one matrix accomodating well. These test devices each had a sample cup resembling the sample cup 47 in test device 10, the axis of which was aligned with longitudinal dimension of said test device rather than being normal thereto as in test device 10. Passage means corresponding to passage 50 in test device 10 provided fluid flow passage means for flow of liquid from the sample cup to one end of the single well, and passage means corresponding to the passage 53 in test device 20 provided for fluid flow from the other end of the single well to an outlet port corresponding to the port 48 in test device 10.

The test devices, when used in the performance of an assay were oriented vertically, with the sample well facing upwardly and the axis of the single well horizontal. The test devices in this example were provided with suitable conduit means for connection of the outlet port to a syringe pump like the pump 86 in FIG. 3, for supplying a vacuum sufficient to draw liquids from the sample cup through the matrix in the single well and out the outlet port. Also used were a light source and instrumentation for taking transmittance measurements horizontally from the matrix of each vertically oriented test device. Four matrices of the presently preferred form most recently described herein were disposed within the respective wells of the test devices. Goat antihuman IgG capture antibodies were bound to the surfaces of the fluid passageways of said matrices for exposure therein.

To this end a solution of the IgG antibodies was prepared by diluting to 50 ml with phosphate buffered saline (Sigma No. 1000-3) 22 microliters of a stock goat antihuman IgG antibody solution(Sigma No. 1-2136). One ml portions of this solution were placed in the sample cup and drawn through the matrices in the respective test device to effects binding of the antibodies to the surface of the nitrocellulose film exposed within the fluid passageways of said matrices. This was followed by drawing from the sample cup and through the matrix of each test device a 1 ml portion of a bovine serum albumin standard blocking solution (Sigma No. 4506) to thereby block the remaining sites on the nitrocellulose film exposed within the fluid passageways of the respective matrices.

Four standard solutions containing respectively different concentrations of human immunologlobulin in phosphate buffered saline were then prepared. For each of these solutions a quantity of dry powder form of human immunoglobulin (Sigma No. 1-4506) was dissolved in enough phosphate buffered saline (Sigma No. 1000-3) to make 50 ml of standard solution having the desired concentration of IgG.

The concentrations of these standard solutions, A through D, were as shown in Table 3 below, which indicates said concentrations in terms of both ng/ml and molar.

TABLE 3

| Solution | Concentration ng/ml | Molar |
|---|---|---|
| A | 1.0 | $6.75 \cdot 10^{-12}$ |
| B | 10 | $6.75 \cdot 10^{-11}$ |
| C | 100 | $6.75 \cdot 10^{-10}$ |
| D | 1000 | $6.75 \cdot 10^{-9}$ |

A one ml portion of each of the four standard solutions was drawn through the matrix of a separate one of the four test devices, causing the human immunoglobulin in said portions to bind to the antihuman IgG capture antibodies exposed within the fluid passageways of the respective matrices.

A solution of IgG:alkaline phosphatase conjugate was prepared by diluting to 50 ml in buffered saline (Sigma No. 1000-3) 25 microliters of IgG:alkaline phosphatase conjugate (Sigma No. A-8542). A one ml portion of this solution was then drawn through the matrix of each of the test devices to cause said conjugate to bind to the human immunoglobulin bound to the capture antibodies within the fluid passageways of the respective matrices. A one ml solution of buffered saline (Sigma 1000-3) was then drawn through the matrix of each device to remove any unbound conjugate.

A solution of a substrate for alkaline phosphatase was made by dissolving, in enough diethanolamine buffer (ph 9.4) to make 50 ml of solution, 1 mg of nitro blue tetrazolium (NBT, Sigma No. N-6639) and 12 mg of 4-bromo-4 chloro-3 indoyl phosphate (BCIP, Sigma No. B-1026). One ml of this substrate solution was drawn through the matrix of one of the four test devices prepared as described above, and transmittance measurements of the involved matrix were taken and recorded before, during and after the flow of the substrate therethrough. When this substrate contacted the alkaline phosphatase within the fluid flow passages of the involved matrix, the alkaline phosphatase catalyzed the development from said substrate of particles of an insoluble, substantially opaque light absorptive colored end product in said passageways. As described earlier herein, contact of particles of the developing substantially opaque colored end product with the reflective granules exposed within the matrix passageways causes a dramatic and rapid decrease in the light scattering coefficient of the contacted granules. This decrease is illustrated by the transmittance data from the respective matrix versus time in seconds, which when plotted, was productive of one of the family of curves shown in FIG. 5.

This procedure was repeated with respect to each of the other three prepared test devices by sequentially drawing a 1 ml portion of the substrate solution through the matrices thereof and recording the changes in transmittance from the respective matrices as described with respect to the first test device. The transmittance data generated was productive of the other three curves shown in FIG. 5.

It will be observed that each of the curves in FIG. 5 exhibits a generally straight line initial portion, the slope of which varies from least to greatest in direct relation to the amount of insoluble substantially opaque colored end product produced in the respective matrices by the concentration of IgG in the respective standard solutions drawn through said matrices. As shown in FIG. 5, the curves tend to taper off in a generally horizontal direction as the measured change in transmittance moderates with time.

Figure 6:
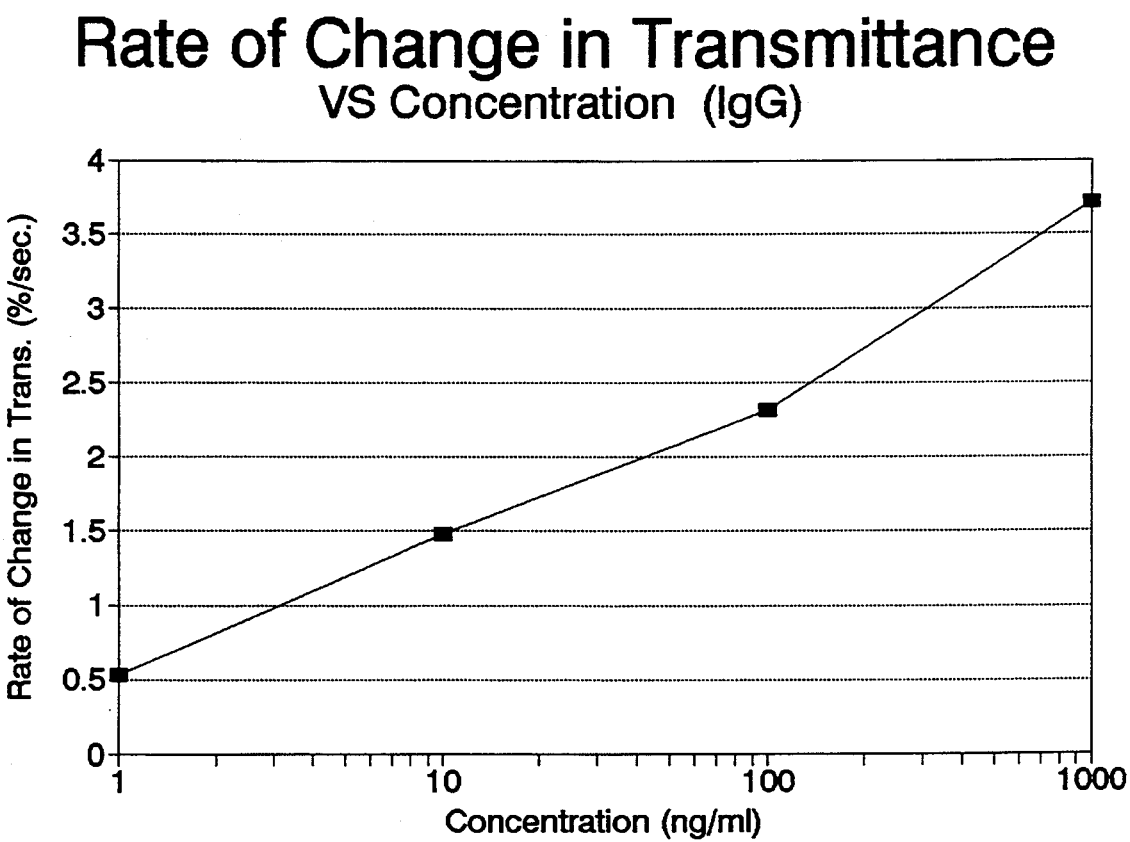
FIG. 6 shows a standard curve produced from the curves in FIG. 5 and illustrating the change in transmittance per second of the matrices represented in FIG. 5 corresponding to the varying concentrations of IgG analyte.

From the curves in FIG. 5 corresponding to known concentrations of IgG in the standard solutions, the standard curve shown in FIG. 6 can be plotted. This is done by extending a tangent to the generally straight line portion of each curve in FIG. 5 down to its intersection with the horizontal axis. Each of these tangents intersects the horizontal axis at a point greater in time, in inverse relation to the amount of insoluble substantially opaque colored end product produced by the concentration of IgG in the standard solutions represented by the respective curves in FIG. 5.

The percent change in transmittance per second is represented by the slope of the tangent to the generally straight line portions of the respective curves in FIG. 5 and is the quotient of 100 divided by the number of seconds indicated at the respective tangent intersection points on the horizontal axis. The standard curve of FIG. 6 was prepared by plotting the thus calculated percent change of transmittance caused by the substantially opaque insoluble colored end product produced by each standard solution as the ordinate and the corresponding concentration of the respective standard solution as the abscissa of the four points defining said curve. As shown on FIG. 6, the respective rates of change of transmittance per second exhibited by the matrices, in the order of increasing concentration of IgG in the respective standard solutions, is about 0.6, 1.5, 2.25 and 3.7 percent per second.

The standard curve shown in FIG. 6 illustrates the rate of change in transmittance produced by any concentration of IgG analyte in a sample within the range of from about 1 to 1000 ng/ml, and it is useful for determining the concentration of IgG analyte in a specimen. This can be done by simply repeating the procedure which was productive of the curves in FIG. 5, using a sample of the specimen to be assayed.

The resultant transmittance data recorded is then plotted as in FIG. 5, and the slope of the initial generally straight line portion of the resulting curve is determined by the point at which the tangent thereto intersects the horizontal axis. Dividing 100 by the number of seconds at the intersection point provides the rate of change in transmittance per second corresponding to the concentration of IgG in the sample assayed. This rate of transmittance change, when transferred to the standard curve of FIG. 6 as an ordinate value, defines a point thereon, the abscissa value of which is the concentration of IgG in the sample assayed.

It will be observed from FIG. 5 that the data necessary for the plotting of the generally straight line portions of all of the curves therein is produced within about 45 seconds of the initiation of flow of the enzyme substrate through each of the involved matrices. Plotting of the curve representing transmittance versus time can be done by computer as the data is generated, or it can be done manually. The change in transmittance per second represented by the slope of the tangent to the generally straight line portion of the developed curve can be determined and transferred to the standard curve of FIG. 6 within minutes, for direct read out of the concentration of IgG in the sample assayed.

By extrapolation of the standard curve in FIG. 6 below the 1 ng/ml plot point, the lowest concentration of IgG which can be detected appears to be about 20 picograms/ml. This corresponds to the point below which the noise level in the electronic portion of the computer caused by flow of substrate through the matrix prevented accurate read out. The noise level in the computer used prevented determination of any transmittance change per second which is below 0.00083 percent.

The high sensitivity with which the invention can detect the development of substantially opaque insoluble colored end product in each matrix, combined with the quick read out of the concentration of analyte in the samples assayed, is a dramatic improvement over the combined sensitivity and speed of read out of currently available techniques which are not as sensitive and which may require hours or even days to obtain a result.

EXAMPLE 2

This example demonstrates the determination of the concentration of T3 in a sample of a fluid specimen. In this example, in which a competitive type immunoassay is performed, six test devices of the type used in Example 1 were used, and the matrices of each were processed by the same procedural steps. The first step of the procedure utilized a suspension in buffer of microbeads of polystyrene or similar material having a size of the order of 1 micron. Capture antibodies of goat anti T3 are bound to the surfaces of these beads which are available commercially as part of IMx Total T3 Reagent Pack, No. 2250-20, sold by Abbott Laboratories, Abbott Park, Ill. 60064.

A 150 microliter portion of this suspension was placed in the sample cup of the first test device and vacuum was applied. This caused the buffer vehicle of the suspension to pass through the matrix, and caused a portion of the microbeads therein to enter the fluid passageways in the matrix of the device. Disposition of the microbeads in said fluid passageways does not, however, adversely restrict fluid flow through said matrix. This step was repeated for each of the other five test devices.

A 150 microliter portion of standard or calibrator solution of T3 was then drawn through the matrices of all of the test devices. The standard solution used for each test device was different from that used in the others, and was selected from those listed below in Table 2. In each case, except for Solution A, the T3 in the standard solution became bound to the capture antibodies on the microbeads with which it came in contact. The number of sites on the microbeads occupied by the standard solution portion were in direct relation to the T3 concentration in the respective standard solutions. The standard or calibrator solutions, prepared in processed bovine serum, are available commercially as the IMx Total T3 Calibrators (Abbott No. 2250-01) in the concentrations indicated below.

TABLE 4

| Solution | Concentration | |
|---|---|---|
| | ng/ml | Molar |
| A | 0.0 | 0.0 |
| B | 0.5 | $.77 \cdot 10^{-12}$ |
| C | 1.0 | $1.54 \cdot 10^{-12}$ |
| D | 2.0 | $3.07 \cdot 10^{-12}$ |
| E | 4.0 | $6.14 \cdot 10^{-12}$ |
| F | 8.0 | $12.12 \cdot 10^{-12}$ |

150 microliters of a T3:alkaline phosphatase conjugate in buffer with protein stabilizers, which is available as a component of the aforementioned IMx Total T3 Reagent Pack, is then drawn through the matrix in each of the respective test devices. This conjugate becomes bound to the remaining available sites on the capture antibody bound to the microbeads in each of the matrices. Any unbound conjugate is then removed by drawing 1 ml of buffered saline (Sigma 1000-3) through the matrices of each test device.

One ml of the NBT/BCIP enzyme substrate solution used in Example 1 was then drawn through the matrix of the first of the six test devices, and the change in transmittance from that matrix caused by formation therein of substantially opaque insoluble colored end product was monitored on a second by second basis beginning with the initiation of the flow of said substrate through that matrix. The same procedure was followed with respect to the remaining five test devices, and the data generated was plotted as the family of six curves shown in FIG. 7. In each case the slope of the tangent to the generally straight line portion of the curve was determined as in Example 1 and the respective transmittance change per second determined therefrom was used to plot the standard curve of FIG. 8.

Figure 7:
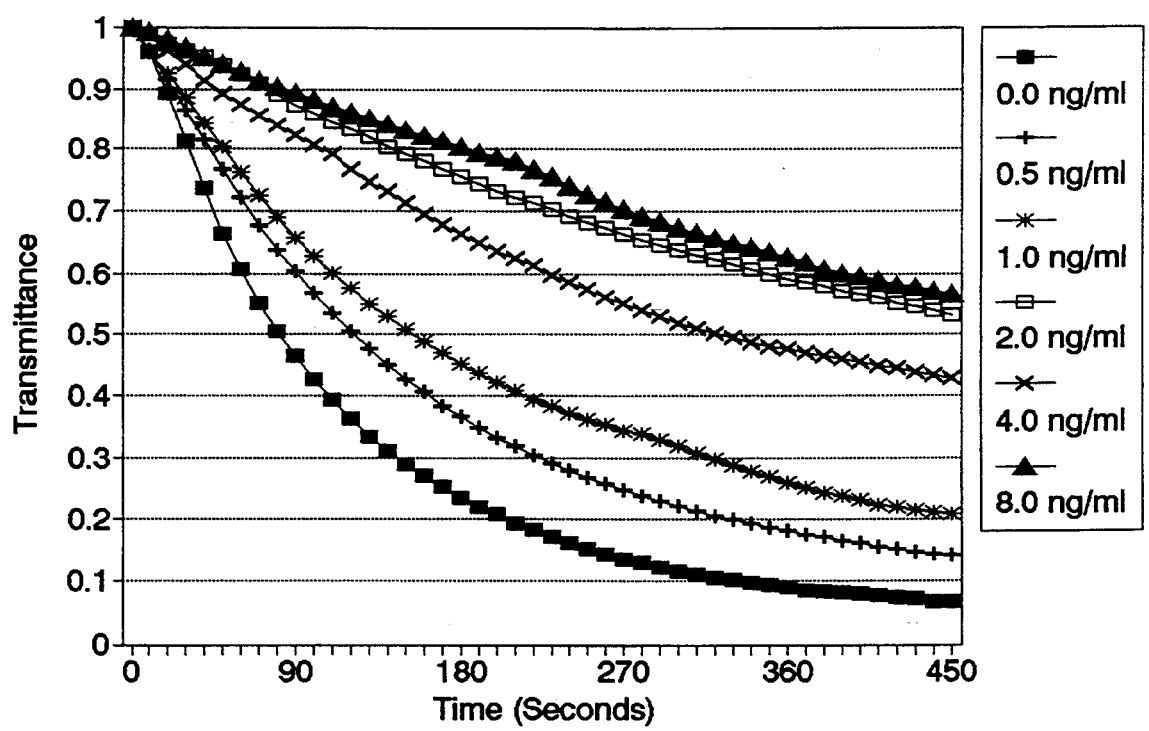
FIG. 7 shows a family of six curves which illustrate the changes in transmittance of matrices of the present invention versus time of formation of particles of substantially opaque insoluble colored end product produced when liquid samples in which T3 (Triiodothyronine) is present in known concentrations of 0, 0.5, 1.0, 2.0, 4.0, and 8.0 nanograms per milliliter, respectively, are assayed.
Figure 8:
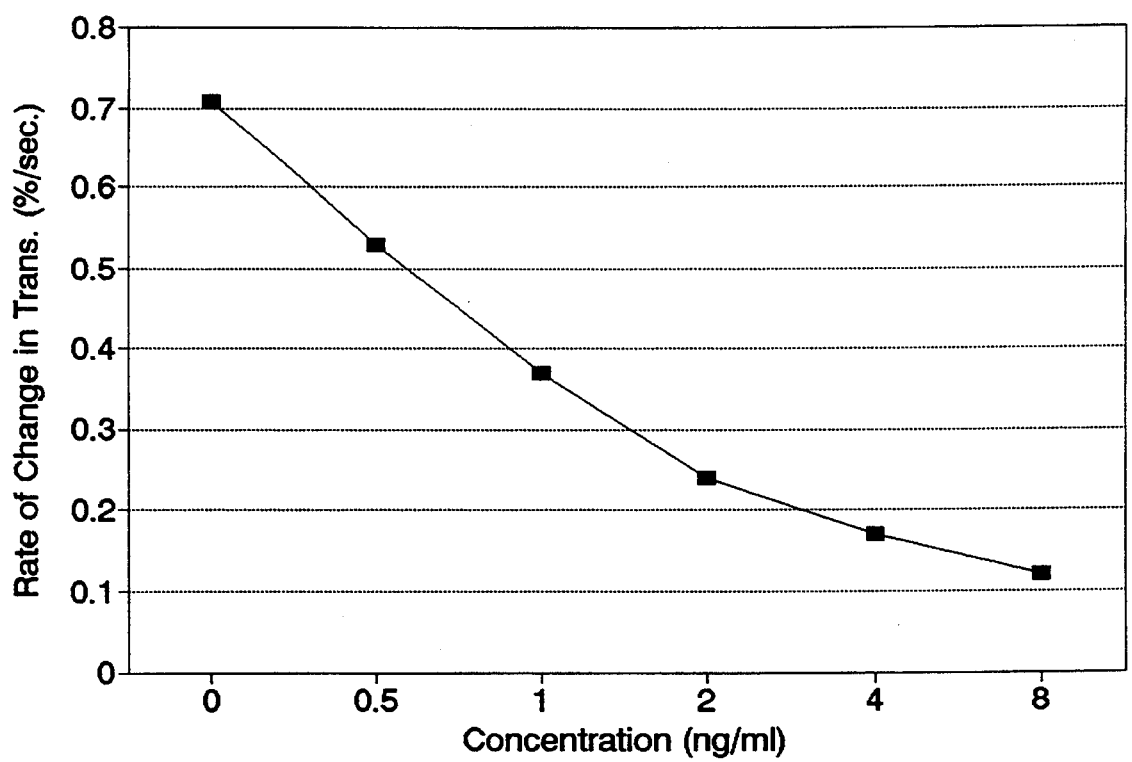
FIG. 8 shows a standard curve produced from the curves in FIG. 7 and illustrating the changes in transmittance per second of the matrices represented in FIG. 7 corresponding to varying concentrations of T3 analyte.

Having in hand the standard curve of FIG. 8. The concentration of T3 in any liquid sample in which the T3 is present in the range of from 0 to 8 ng/ml can be readily determined by repeating, with that sample, the procedure described for the generation of the curves in FIG. 7. As in Example 1, the slope of the tangent to the generally straight line portion of the thereby generated transmittance versus time curve is used to determine the transmittance change per second caused by the T3 in the sample. This rate of transmittance change, when transferred to the standard curve of FIG. 8 as an ordinate value, defines a point thereon, the abscissa value of which is the concentration of T3 in the sample.

The standard curve of FIG. 8 has a slope which is the reverse of the standard curve in FIG. 6. This is because, in a competitive assay, when the amount of T3 in the sample assayed is small, there are many sites which remain available on the capture antibody coating the microbeads for the T3:alkaline phosphatase conjugate to bind to after the sample has contacted the capture antibody. As a result, a relatively large amount of the conjugate binds to those available sites when it contacts the microbeads. Therefore, when the substrate contacts the relatively large amount of bound alkaline phosphatase, the production of a large amount of insoluble colored end product is catalyzed by the latter, which end product effects a relatively large change in transmittance per second from the involved matrix.

Conversely, when the T3 in the sample assayed is large, there are many fewer sites on the capture antibody available for the alkaline phosphatase conjugate to bind to after the sample has contacted the capture antibody. The smaller amount of alkaline phosphatase which binds to those available sites, catalyzes a relatively smaller amount of insoluble colored end product when contacted by the substrate, which reduced amount of end product produces a relatively smaller transmittance change per second from the involved matrix.

As can be seen from the curves in FIG. 7, the relatively straight line portions of all of said curves are created within about 70 seconds of the initiation of flow of the enzyme substrate through each of the involved matrices. Hence, the measurement of the transmittance change produced by a T3 analyte within the range of 0 to 8 ng/ml can be discontinued after about 70 seconds, and the concentration of said analyte can then be quickly determined by following the procedure described above.

The instrument 65 lends itself well to automated performance of the assays described herein. Those skilled in the art will recognize that a suitable electromechanical or other type operator can be provided for each of the valves 94 to 97, 101 to 103 and 105, and that operation of such valves, together with operation of the syringe pump 86 and vacuum pump 87, can be readily placed under the control of a computerized system programmed to carry out in proper sequence each step of the assay procedures described herein.

Various other changes, modifications and amplifications can be made in the test device, matrices, instrument and method disclosed herein without departing from the spirit of the invention, and all of such changes are contemplated as may come within the scope of the claims appended hereto.

What is claimed is:

1. A light transmittance type analytical system for rapid detection of minute amounts of an insoluble substantially opaque colored light absorptive product, said system comprising an optical component comprising a fluid and light permeable matrix of compacted reflective granules which have a light scattering coefficient of at least about eighty that is reducible by contact of said granules by said product, said granules having a light absorption coefficient of substantially zero, there being interstices between adjacent granules of said matrix; means for causing the formation of an insoluble substantially opaque colored light absorptive product in the interstices of at least a portion of said matrix; means for subjecting said matrix to incident light; and means for monitoring the change in the light transmittance of said matrix caused by the combined effect of direct absorption of light by said product and concomitant reduction of the light scattering coefficient of granules in said matrix contacted by particles of said product.

2. A variable light transmittance optical system component useful in a light transmittance system for the rapid detection of minute amounts of an insoluble substantially opaque light absorptive colored product in a light transmissive fluid specimen, said component comprising a matrix of compacted reflective granules having a light absorption coefficient of substantially zero and a light scattering coefficient of at least about eighty, at least one of which coefficients is changed by contact of particles of and insoluble substantially opaque colored product with said granules, said matrix having interstices between adjacent granules therein providing passage means for flow therethrough of a fluid specimen, said matrix exhibiting a first level of light transmittance capability when a light transmissive fluid specimen disposed in said passage means is devoid of said insoluble substantially opaque light absorptive colored product, said matrix exhibiting a substantially reduced light transmittance capability when there is present in such specimen particles of and an insoluble substantially opaque light absorptive product which contacts granules of said matrix, such reduction in the light transmittance capability of said matrix being caused by the combined effect of the light absorptive character of said product and the change in said at least one coefficient caused by contact of particles of said product with said granules.

3. The optical system component of claim 2 wherein said matrix granules are selected from the group consisting of aluminum oxide, barium sulfate and polystyrene.

4. The optical system component of claim 2 wherein said matrix also comprises carrier granules capable of having an analyte capture substance bound thereto, which carrier granules are selected from the group consisting of polystyrene, nitrocellulose, derivitized nylon, glass and certain of said matrix granules which are coated with nitrocellulose.

5. The optical system component of claim 2 wherein at least some of the granules in said matrix are coated with a film of nitrocellulose.

6. The optical system component of claim 2 wherein the matrix interstices provide a multiplicity of fluid flow passage means through said matrix.

7. A test device comprising the optical system component of claim 2 and a carrier therefor.

8. The test device of claim 7 wherein said carrier is formed with at least one well in which said matrix is accommodated, said well having a side wall which is nontransmissive of light and is reflective thereof.

9. The test device of claim 7 wherein said carrier is formed with a plurality of wells each of which accomodates one of said matrices, said carrier being formed with fluid flow passage means communicating with said plurality of wells.

10. The test device of claim 9 wherein each of said matrices comprises a capture substance specific for a particular analyte and which is exposed within the fluid passage means thereof.

11. The optical system component of claim 2 wherein said granules have a size in the range of from about 5 microns to about 300 microns.

12. The optical system component of claim 2 wherein it is the light scattering coefficient of said granules which is changed by contact of particles of an insoluble substantially opaque colored product therewith.

13. A light transmittance type analytical system for the rapid detection of minute amounts of an insoluble substantially opaque colored light absorptive product in a fluid specimen, said system comprising a variable light transmittance optical component formed of a matrix of compacted reflective granules having a light absorption coefficient of substantially zero and a light scattering coefficient of at least about eighty, at least one of which coefficients is changed by contact of particles of an insoluble substantially opaque colored product with said granules, said matrix having interstices between adjacent granules therein providing passage means for flow therethrough of a fluid specimen, said matrix exhibiting a first level of light transmittance capability when a light transmissive fluid specimen disposed in said passage means is devoid of an insoluble substantially opaque light absorptive colored product, said matrix exhibiting a substantially reduced light transmittance capability when there is present in such fluid specimen particles of an insoluble substantially opaque light absorptive colored product which contact granules of said matrix, such reduction in the light transmittance capability of said matrix being caused by the combined effect of the light absorptive character of said product and the change in said at least one coefficient caused by contact of particles of said product with said granules; means for subjecting said matrix to incident light; and means for monitoring the change in light transmittance capability of said matrix produced by the presence in a fluid specimen in said passage means of particles of an insoluble substantially opaque colored product which contact granules of said matrix.

14. The analytical system of claim 13 wherein said granules have a size in the range of from about 5 microns to about 300 microns.

15. The analytical system of claim 13 wherein it is the light scattering coefficient of said granules which is changed by contact of particles of said insoluble substantially opaque colored product therewith.

16. The analytical system of claim 13 wherein said matrix granules are selected from the group consisting of aluminum oxide barium sulfate and polystyrene.

17. The analytical system of claim 13 wherein said matrix also comprises carrier granules capable of having an analyte capture substance bound thereto, which carrier granules are selected from the group consisting of polystyrene, nitrocellulose, derivitized nylon, glass and certain of said matrix granules which are coated with nitrocellulose.

18. The analytical system of claim 13 wherein at least some of the granules in said matrix are coated with a film of nitrocellulose.

19. The analytical system of claim 13 wherein said matrix interstices provide a multiplicity of fluid flow passage means through said matrix.

20. The analytical system of claim 13 wherein said optical component is supported on a carrier therefor.

21. The analytical system of claim 20 wherein said carrier is formed with at least one well in which said matrix is accommodated, said well having a side wall which is nontransmissive of light and is reflective thereof.

22. The analytical system of claim 20 wherein said carrier is formed with a plurality of wells each of which accommodates one of said matrices, said carrier being formed with fluid flow passage means communicating with said plurality of wells.

23. The analytical system of claim 22 wherein each of said matrices comprises a capture substance specific for a particular analyte.

24. The analytical system of claim 23 wherein a plurality of said matrices respectively comprise capture substances which are specific for different analytes.

25. The optical system component of claim 2 wherein contact of particles of an insoluble substantially opaque colored product with said granules causes reduction of the light scattering coefficient thereof.

26. The optical system of claim 13 wherein contact of particles of an insoluble substantially opaque colored product with said granules causes reduction of the light scattering coefficient thereof.

27. A light transmittance type analytical system for detection of minute amounts of an insoluble substantially opaque colored light absorptive substance, said system comprising a variable light transmittance optical component comprising a matrix of reflective granules having a light absorption coefficient of substantially zero and a light scattering coefficient of at least about eighty, at least one of said coefficients being changeable by contact of said reflective granules by such substance; means for causing particles of such substance to contact reflective granules of said optical component; means for subjecting said optical component to incident light; and means for measuring the change in light transmittance of said optical component caused by the combined effect of absorption of light by said substance and the change in said at least one coefficient of the granules contacted by said substance.

28. A variable light transmittance optical component for use in a light transmittance type system for the detection of minute amounts of an insoluble substantially opaque light absorptive colored substance, said component comprising a matrix of reflective granules having a light absorption coefficient of substantially zero and a light scattering coefficient of at least about eighty, whereby said optical component exhibits a first level of light transmittance capability, at least one of said coefficients being changeable by contact of said reflective granules by particles of said substance, which contact causes said optical component to exhibit a substantially different second level of light transmittance capability due to the combined effect of the light absorptive character of said substance and the change in said at least one coefficient caused by contact of said substance with said reflective granules.

29. A light transmittance type analytical system for detection of minute amounts of an insoluble substantially opaque light absorptive substance in a fluid specimen, said system comprising a variable light transmittance optical component formed of a matrix of reflective granules having a light absorption coefficient of substantially zero and a light scattering coefficient of at least about eighty, whereby said component exhibits a first level of light transmittance capability when a light transmissive fluid specimen in contact therewith is devoid of said substance, the light scattering coefficient of said granules being reduced by contact of particles of said substance with said reflective granules, which contact causes said component to exhibit a substantially reduced second level of light transmittance capability due to the combined effect of the light absorptive character of said substance and the reduction in the light scattering coefficient of said granules caused by contact of said particles therewith means for subjecting said component to incident light; and means for measuring the change in the light transmittance capability of said component produced by the presence in a fluid specimen of particles of said substance which contact reflective granules of said component.

30. A variable light transmittance optical component for use in a light transmittance type system for the detection of minute amounts of an insoluble substantially opaque light absorptive colored substance, said component comprising a matrix of reflective granules having a light absorption coefficient of substantially zero and a light scattering coefficient of at least about eighty, the light scattering coefficient of said granules being changeable by contact of said substance therewith, such change in light scattering coefficient, together with the light absorptive character of said substance, effecting a measurable change in the light transmittance capability of said component.

31. The variable light transmittance optical component of claim 30 wherein both the light scattering coefficient of said granules and the light transmittance capability of said component are reduced upon contact of said reflective granules by said substance.

32. The optical system component of claim 30 wherein certain of said reflective granules have means for binding an analyte capture substance thereto.

33. The optical system component of claim 30 wherein substantially all of the reflective granules in said matrix have means for binding an analyte capture substance thereto.

34. The optical system component of claim 32 wherein said analyte capture substance comprises nucleic acid sequences complementary to target sequences in an analyte to be detected.

35. The optical component of claim 32 wherein said analyte capture substance comprises capture antibodies reactive to selected antigens in an analyte to be detected.

36. A test device comprising the optical system component of claim 30 and a carrier therefor.

37. The test device of claim 36 wherein the carrier is formed with at least one well in which said optical component is accommodated, said well having a sidewall which is nontransmissive of light and is reflective thereof.

38. The test device of claim 36 wherein said carrier is formed of a plurality of said wells, each of which accommodates one of said optical components, said carrier being provided with fluid flow passage means communicating with said wells.

39. The test device of claim 38 wherein each of said optical components comprises a capture substance specific for a particular analyte.

40. The test device of claim 36 wherein certain of the reflective granules in said optical component have means for binding an analyte capture substance thereto.

41. The test device of claim 36 wherein substantially all of the reflective granules in said optical component have means for binding an analyte capture substance thereto.

42. The test device of claim 40 wherein said analyte capture substance comprises nucleic acid sequences complementary to target sequences in an analyte to be detected.

43. The test device of claim 40 wherein said analyte capture substance comprises capture antibodies reactive to selected antigens in an analyte to be detected.

* * * * *